(12) United States Patent
Verwaal et al.

(10) Patent No.: US 9,340,804 B2
(45) Date of Patent: May 17, 2016

(54) DICARBOXYLIC ACID PRODUCTION IN EUKARYOTES

(75) Inventors: René Verwaal, Nootdorp (NL); Liang Wu, Delft (NL); Robbertus Antonius Damveld, Berkel en Rodenrijs (NL); Cornelis Maria Jacobus Sagt, Utrecht (NL)

(73) Assignee: DSM IP ASSETS B.V., Heerlen (NL)

( * ) Notice: Subject to any disclaimer, the term of this patent is extended or adjusted under 35 U.S.C. 154(b) by 537 days.

(21) Appl. No.: 12/743,927

(22) PCT Filed: Nov. 14, 2008

(86) PCT No.: PCT/EP2008/065588
§ 371 (c)(1),
(2), (4) Date: Sep. 15, 2010

(87) PCT Pub. No.: WO2009/065780
PCT Pub. Date: May 28, 2009

(65) Prior Publication Data
US 2011/0081694 A1  Apr. 7, 2011

(30) Foreign Application Priority Data

| | | | |
|---|---|---|---|
| Nov. 20, 2007 | (EP) | ................................. | 07121113 |
| Nov. 20, 2007 | (EP) | ................................. | 07121117 |
| Nov. 20, 2007 | (EP) | ................................. | 07121120 |
| May 27, 2008 | (EP) | ................................. | 08156959 |
| May 27, 2008 | (EP) | ................................. | 08156960 |
| May 27, 2008 | (EP) | ................................. | 08156961 |

(51) Int. Cl.
| | |
|---|---|
| *C12N 1/14* | (2006.01) |
| *C12N 9/88* | (2006.01) |
| *C12N 15/00* | (2006.01) |
| *C12N 1/20* | (2006.01) |
| *C07H 21/04* | (2006.01) |
| *C12P 7/44* | (2006.01) |
| *C12P 7/46* | (2006.01) |
| *C12N 15/81* | (2006.01) |
| *C12N 9/02* | (2006.01) |

(52) U.S. Cl.
CPC . *C12P 7/46* (2013.01); *C12N 9/001* (2013.01); *C12N 9/88* (2013.01); *C12N 15/81* (2013.01); *C12N 15/815* (2013.01); *Y02P 20/52* (2015.11)

(58) Field of Classification Search
CPC ........ C12N 9/88; C12N 15/81; C12N 15/815; C12P 7/46
See application file for complete search history.

(56) References Cited

U.S. PATENT DOCUMENTS

| | | | |
|---|---|---|---|
| 4,828,993 | A | 5/1989 | Sridhar |
| 5,643,758 | A | 7/1997 | Guan et al. |
| 2006/0246560 | A1 | 11/2006 | Fatland-Bloom et al. |
| 2007/0042477 | A1 | 2/2007 | Lee et al. |

FOREIGN PATENT DOCUMENTS

| | | |
|---|---|---|
| EP | 1 672 077 A1 | 6/2006 |
| EP | 1 867 727 A1 | 12/2007 |
| WO | WO 2006/083410 A2 * | 8/2006 |
| WO | 2007/019301 | 2/2007 |
| WO | 2007/030830 | 3/2007 |
| WO | 2007/061590 | 5/2007 |
| WO | 2008144626 | 11/2008 |
| WO | 2009/011974 A1 | 1/2009 |
| WO | 2009011974 | 1/2009 |
| WO | 2014/043591 A1 | 3/2014 |

OTHER PUBLICATIONS

Q6w6x5—UniProtKB/TrEMBL Database. 2007.*
Patil et al. Evolutionary programming as a platform for in silico metabolic engineering. BMC Bioinformatics. Dec. 23, 2005;6:308.*
Warnecke et al. Organic acid toxicity, tolerance, and production in *Escherichia coli* biorefining applications. Microb. Cell Fact. 4:25. 2005.*
Romanos et al. Foreign Gene Expression in Yeast: a Review. Yeast vol. 8:423-488 (1992).*
Stewart et al. Biotechnology and Genetic Engineering Reviews, 14:67-143, 1997.*
UnitProt Database—retrieved from the internet via http://www.uniprot.org on Feb. 11, 2013.*
Co-pending U.S. Appl. No. 12/743,416, filed May 18, 2010; WO 2009/065777.
Co-pending U.S. Appl. No. 12/743,106, filed May 14, 2010; WO 2009/065778.
Co-pending U.S. Appl. No. 12/743,652, filed May 19, 2010; WO 2009/065779.
International Search Report for PCT/EP2008/065582, mailed Feb. 12, 2009.
International Search Report for PCT/EP2008/065583, mailed Feb. 12, 2009.
International Preliminary Report on Patentability for PCT/EP2008/065583, mailed Mar. 12, 2010.
International Search Report for PCT/EP2008/065587, mailed Feb. 12, 2009.
Written Opinion of the International Searching Authority for PCT/EP2008/065587, mailed Feb. 12, 2009.
Database UniProt [online], Apr. 12, 2005, "Mitochondrial NADH-Dependent Fumarate Reductase (EC 1.3.1.6)." XP002477927.
Database UniProt [online], Mar. 1, 2003, "NADH-Dependent Fumarate Reductase." XP002477928.

(Continued)

*Primary Examiner* — Yong Pak
(74) *Attorney, Agent, or Firm* — McBee Moore Woodward & Vanik IP, LLC

(57) ABSTRACT

The present invention relates to a recombinant eukaryotic microbial cell comprising a nucleotide sequence encoding a heterologous enzyme catalyzing the conversion from phosphoenolpyruvate to oxaloacetate whereby ATP is generated. The invention further relates to a process for the preparation of a dicarboxylic acid such as succinic acid and fumaric acid, comprising fermenting the eukaryotic microbial cell according to the invention in a suitable fermentation medium.

15 Claims, 15 Drawing Sheets

(56) References Cited

OTHER PUBLICATIONS

Database UniProt [Online], Accession No. A2R097, (Mar. 6, 2007), 2 pages. XP-002477243.
Database UniProt [Online], "Aspergillus niger contig An12c0260, complete genome.", Accession No. AM270282, (Jan. 28, 2007), 28 pages. XP-002477242.
Database UniProt [online] Oct. 1, 1996, "Fumarate Hydratase, Mitochondrial Precursor (EC 4.2.1.2) (Fumarase)." XP002477029.
Database UniProt [online], Sep. 11, 2007, "Fumarase." XP002477030.
Database UniProt [online], Oct. 1, 1993, "Fumarate Recuctase (NADH) (EC 1.3.1.6) (NADH-dependent Fumarate Reductase) (FAD-Dependent Oxidoreductase FRDS)." XP002477929.
Friedberg, D., et al, "The *fumR* gene encoding fumarase in the filamentous fungus *Rhizopus oryzae*: cloning, structure and expression", Gene, vol. 163, No. 1, (Sep. 22, 1995), pp. 139-144.
Pines et al.; "The Cytosolic Pathway of L-malic Acid Synthesis in *Saccharomyces cerevisiae*: The Role of Fumarase", Applied Microbiology and Biotechnology, vol. 46, No. 4, 1996, pp. 393-399, XP008090537.
Peleg et al.; "Inducible Overexpression of the FUM1 Gene in *Saccharomyces cerevisiae*: Localization of Fumarase and Efficient Fumaric Acid Bioconversion to L-malic Acid", Applied and Environmental Microbiology, vol. 56, 1990, pp. 2777-2783, XP002408560.
Coustou et al.; "A Mitochondrial NADH-dependent Fumarate Reductase Involved in the Production of Succinate Excreted by Procyclic Trypanosoma Brucei", Journal of Biological Chemistry, vol. 280, No. 17, Apr. 2005, pp. 16559-16570, XP002477924.
Enomoto et al.; "Physiolocial Role of Soluble Fumarate Recuctase in Redox Balancing during Anaerobiosis in *Saccharomyces cerevisiae*", FEMS Microbiology Letters, vol. 215, No. 1, Sep. 24, 2002, pp. 103-108, XP002477926.
Besteiro et al.; "Succinate Secreted by Trypanosoma Brucei is Produced by a Novel and Unique Glycosomal Enzyme, NADH-dependent Fumarate Reductase." Journal of Biological Chemistry, vol. 277, No. 41, Oct. 11, 2002, pp. 38001-38012, XP002477925.
International Search Report for PCT/EP2008/065588, mailed Feb. 12, 2009.
Written Opinion of the International Searching Authority, for PCT/EP2008/065588, mailed Feb. 12, 2009.
Jacob et al., "Fast High-Performance Liquid Chromatographic Purification of *Saccharomyces cerevisiae* Phosphoenolpyruvate Carboxykinase.", Journal of Chromatography, vol. 625, No. 1, Nov. 13, 1992, pp. 47-54, XP008091044.
Bauer et al., "By-Product Formation during Exposure of Respiring *Saccharomyces cerevisiae* Cultures to Excess Glucose is not caused by a Limited Capacity of Pyruvate Carboxylase", FEMS Microbiology Letters, vol. 179, No. 1, Oct. 1, 1999, pp. 107-113, XP002478740.
Millard et al., "Enhanced Production of Succinic Acid by Overexpression of Phosphoenolpyruvate Carboxylase in *Escherichia coli*", Applied and Environmental Microbiology, Washington, DC, US, vol. 62, No. 5, May 1, 1996, pp. 1808-1810, XP002132795.

Lin et al., "Metabolic Engineering of Aerobic Succinate Production Systems in *Escherichia coli* to Improve Process Productivity and Achieve the Maximum Theoretical Succinate Yield", Metabolic Engineering, vol. 7, No. 2, Mar. 2005, pp. 116-127, XP004801711.
De Jongh et al., "Enhanced Citrate Production through Gene insertion in Aspergillus Niger", Metabolic Engineering, vol. 10, No. 2, Nov. 17, 2007, pp. 87-96, XP022510142.
De Jongh "Organic Acid Production by Aspergillus Niger", PHD Thesis, May 2006, pp. I-109, XP002445685.
Kubo et al., "Effect of Gene Disruption of Succinate Dehydrogenase on Succinate Production in a Sake Yeast Strain", Journal of Bioscience and Bioengineering, vol. 90, No. 6, 2000, pp. 619-624, XP003009625.
Song et al., "Production of Succinic Acid by Bacterial Fermentation", Enzyme and Microbial Technology, vol. 39, No. 3, Jul. 3, 2006, pp. 352-361, XP005459365.
Goldberg et al., "Organic Acids: old Metabolites, New Themes", Journal of Chemical Technology and Biotechnology, vol. 81, No. 10, Oct. 2006, pp. 1601-1611, XP002477014.
International Preliminary Report on Patentability for PCT/EP2008/065588, mailed Mar. 12, 2010.
Abe et al. (Mycopath. 2006, vol. 162, pp. 143-153).
Fujimaki et al., "Processability and properties of aliphatic polyesters, 'BIONOLLE', synthesized by polycondensation reaction", Polymer Degradation and Stability, Barking, GB vol. 59, No., 1-3, Jan. 3, 1998, pp. 209-214, XP027153158, ISSN: 0141-3910.
European Search Report corresponding to European Patent Application No. 13170415.7 dated Jan. 7, 2014.
May et al., "The Importance of Fungi to Man", Genome Research, (1997), vol. 7, pp. 1041-1044.
Wakai et al., "Formation of succinate during fermentation of sake mash and grape must", Brewing Technology (1980), 2 vol. 58, No. 5, pp. 363-368 [Japanese Original and English Translation].
Flores et al., "Carbohydrate and energy-yielding metabolism in non-conventional yeasts", FEMS Microbiology Reviews, (2000), vol. 24, pp. 507-529.
Karniely et al., "Single translation-dual destination: mechanisms of dual protein targeting in eukaryotes", EMBO Reports, (2005) vol. 6., No. 5, pp. 420-425.
Nobel et al., Protein promiscuity and its implications for biotechnology, Nature Biotechnology, (Feb. 9, 2009), vol. 27, No. 2, pp. 157-167.
Vallon et al., "New Sequence Motifs in Flavoproteins: Evidence for Common Ancestry and Tools to Predict Structure", (2000), Proteins: Structure, Function and Genetics, vol. 38, pp. 95-114.
Camarasa et al., Role in anaerobiosis of the isoenzymes for *Saccharomyces cerevisiae* fumarate reductase encoded by OSMI and FRDSI, Wiley Interscience, Mar. 7, 2007, pp. 391-401, Sciences pour l'Oenologie, INRA, Montpellier, France.
Chica et al., Curr Opin Biotechnol. Aug. 2005; 16(4):378-84.
Sen et al., Appl Biochem Biotechnol. Dec. 2007; 143(3):212-23.
Copeland et al., "Phosphoenolpyruvate carboxykinase [*Actinobacillus succinogenes* 130Z]" NCBI: YP_001343536 (WP_011978877) (Dec. 2014).

* cited by examiner

DICARBOXYLIC ACID PRODUCTION IN EUKARYOTES

This application is the U.S. national phase of International Application No. PCT/EP2008/065588, filed 14 Nov. 2008, which designated the U.S. and claims priority to European Application No(s). 07121120.5, filed 20 Nov. 2007, 07121117.1, filed 20 Nov. 2007, 07121113.0, filed 20 Nov. 2007, 08156960.0, filed 27 May 2008, 08156961.8, filed 27 May 2008 and 08156959.2, filed 27 May 2008, the entire contents of each of which are hereby incorporated by reference.

The present invention relates to a recombinant eukaryotic cell comprising a nucleotide sequence encoding an enzyme that catalyses the conversion of phosphoenolpyruvate to oxaloacetate, and a process for the production of a dicarboxylic acid.

The 4-carbon dicarboxylic acids malic acid, fumaric acid and succinic acid are potential precursors for numerous chemicals. For example, succinic acid can be converted into 1,4-butanediol (BDO), tetrahydrofuran, and gamma-butyrolactone. Another product derived from succinic acid is a polyester polymer which is made by linking succinic acid and BDO.

Succinic acid is predominantly produced through petrochemical processes by hydrogenation of butane. These processes are considered harmful for the environment and costly. The fermentative production of succinic acid may be an attractive alternative process for the production of succinic acid, wherein renewable feedstock as a carbon source may be used.

A number of different bacteria such as *Escherichia coli*, and the rumen bacteria *Actinobacillus, Anaerobiospirillum, Bacteroides, Mannheimia*, or *Succinimonas*, sp. are known to produce succinic acid. Metabolic engineering of these bacterial strains have improved the succinic acid yield and/or productivity, or reduced the by-product formation.

WO2007/061590 discloses a pyruvate decarboxylase negative yeast for the production of malic acid and/or succinic acid which is transformed with a pyruvate carboxylase enzyme or a phosphoenolpyruvate carboxylase, a malate dehydrogenase enzyme, and a malic acid transporter protein (MAE).

Despite the improvements that have been made in the fermentative production of dicarboxylic acid, there remains a need for improved microorganisms for the fermentative production of dicarboxylic acids.

The aim of the present invention is an alternative eukaryotic microorganism for the production of a dicarboxylic acid.

The aim is achieved according to the invention with a recombinant eukaryotic microbial cell comprising a nucleotide sequence encoding an enzyme catalysing the conversion from phosphoenolpyruvate to oxaloacetate whereby ATP is generated, wherein the enzyme comprises an amino acid sequence which has at least 50% sequence identity with the amino acid sequence of SEQ ID NO: 1, SEQ ID NO: 3 and/or SEQ ID NO: 5.

Preferably, the enzyme has phosphoenolpyruvate carboxykinase activity, preferably the enzyme is a phosphoenolpyruvate (PEP) carboxykinase (E.C. 4.1.1.49). Preferably, the PEP carboxykinase is active under anaerobic or oxygen limited conditions in the presence of a fermentable carbon source or glycerol. A fermentable carbon source may be glucose, fructose, galactose, raffinose, arabinose, or xylose. It was found advantageous that the eukaryotic cell comprises a PEP carboxykinase according to the present invention, since PEP carboxykinase catalysing the conversion from PEP to OAA fixates $CO_2$ and generates energy in the form of ATP.

Surprisingly, it was found that a recombinant eukaryotic cell according to the present invention produces an increased amount of dicarboxylic acid, such as succinic acid and fumaric acid as compared to the amount of dicarboxylic acid produced by a wild-type eukaryotic cell. Preferably, a eukaryotic cell according to the present invention produces at least 1.2, preferably at least 1.5, 1.6, 1.8 preferably at least 2 times more of a dicarboxylic acid than a wild-type eukaryotic cell which does not comprise the nucleotide sequence encoding an enzyme catalysing the conversion from phosphoenolpyruvate to oxaloacetate of the invention.

Preferably, a eukaryotic microbial cell according to the present invention expresses a nucleotide sequence encoding an enzyme having PEP carboxykinase activity, preferably a PEP carboxykinase wherein the PEP carboxykinase comprises an amino acid sequence that has at least 55%, preferably at least 60, 65, 70, 75, 80, 85, 90, 92, 94, 95, 96, 97, 98, or 99% sequence identity with the amino acid sequence of SEQ ID NO: 1, SEQ ID NO: 3 and/or SEQ ID NO: 5. Preferably the PEP carboxykinase comprises SEQ ID NO: 1, SEQ ID NO: 3 and/or SEQ ID NO: 5.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extension 1, Blosum 62 matrix.

A nucleotide sequence encoding an enzyme expressed in the cell of the invention may also be defined by their capability to hybridise with nucleotide sequences encoding an enzyme having PEP carboxykinase activity of SEQ ID NO.'s: 1, 3 and/or 5, or with the nucleotide sequence encoding an malate dehydrogenase of SEQ ID NO: 14 or with the nucleotide sequence encoding fumarase of SEQ ID NO: 16, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC (sodium chloride, sodium citrate) or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequence of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

A recombinant eukaryotic microbial cell according to the present invention is defined herein as a cell which contains, or is transformed or genetically modified with a nucleotide sequence that does not naturally occur in the eukaryotic cell, or it contains additional copy or copies of an endogenous nucleic acid sequence. A wild-type eukaryotic cell is herein defined as the parental cell of the recombinant cell.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

The term "enzyme" as used herein is defined as a protein which catalyses a (bio)chemical reaction in a cell.

To increase the likelihood that the introduced enzyme is expressed in active form in a eukaryotic cell of the invention, the corresponding encoding nucleotide sequence may be adapted to optimise its codon usage to that of the chosen eukaryotic host cell. Several methods for codon optimisation are known in the art. A preferred method to optimise codon usage of the nucleotide sequences to the eukaryotic cell according to the present invention is codon pair optimization technology as disclosed in WO2008/000632. Codon-pair optimization is a method for producing a polypeptide in a host cell, wherein the nucleotide sequences encoding the polypeptide have been modified with respect to their codon-usage, in particular the codon-pairs that are used, to obtain improved expression of the nucleotide sequence encoding the polypeptide and/or improved production of the polypeptide. Codon pairs are defined as a set of two subsequent triplets (codons) in a coding sequence.

Usually, a nucleotide sequence encoding an enzyme, such as an enzyme having PEP carboxykinase activity, or any other enzyme disclosed herein is operable linked to a promoter that causes sufficient expression of the corresponding nucleotide sequence in the eukaryotic cell according to the present invention to confer to the cell the ability to produce a dicarboxylic acid.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

A promoter that could be used to achieve expression of a nucleotide sequence coding an enzyme, eg. an enzyme having PEP carboxykinase activity may be not native to the nucleotide sequence coding for the enzyme to be expressed, i.e. a promoter that is heterologous to the nucleotide sequence (coding sequence) to which it is operably linked. Preferably, the promoter is homologous, i.e. endogenous to the host cell.

Suitable promoters in eukaryotic host cells are known to the skilled man in the art. Suitable promoters may be, but are not limited to TDH, LPDA, GAL7, GAL10, or GAL 1, CYC1, HIS3, ADH1, PGL, PH05, GAPDH, ADC1, TRP1, URA3, LEU2, ENO, TPI, and AOX1. Other suitable promoters include PDC, GPD1, PGK1, and TEF1.

Usually a nucleotide sequence encoding an enzyme comprises a terminator. Any terminator, which is functional in the cell, may be used in the present invention. Preferred terminators are obtained from natural genes of the host cell. Suitable terminator sequences are well known in the art. Preferably, such terminators are combined with mutations that prevent nonsense mediated mRNA decay in the host cell of the invention (see for example: Shirley et al., 2002, Genetics 161: 1465-1482).

In a preferred embodiment, a nucleotide sequence encoding an enzyme, such as an enzyme having PEP carboxykinase activity is overexpressed. It was found that an increased production of malic acid, fumaric acid or succinic acid by the cell may be achieved when the nucleotide sequences are overexpressed.

There are known methods in the art for overexpression nucleotide sequences encoding enzymes. A nucleotide sequence encoding an enzyme may be overexpressed by increasing the copy number of the gene coding for the enzyme in the cell, e.g. by integrating additional copies of the gene in the cell's genome, by expressing the gene from a centromeric vector, from an episomal multicopy expression vector or by introducing an (episomal) expression vector that comprises multiple copies of one or more gene(s). Preferably, overexpression of a nucleotide sequence encoding an enzyme according to the invention is achieved with a (strong) constitutive promoter.

The invention also relates to a nucleotide construct comprising one or more nucleotide sequence(s) selected from SEQ ID NO: 7, SEQ ID NO: 8, SEQ ID NO: 9 and SEQ ID NO: 10.

A nucleotide sequence encoding an enzyme may be ligated into a nucleic acid construct, for instance a plasmid, such as a low copy plasmid or a high copy plasmid. The eukaryotic cell according to the present invention may comprise a single, but preferably comprises multiple copies of the nucleotide sequence encoding an enzyme that catalyses the conversion of PEP to OAA, for instance by multiple copies of a nucleotide construct.

A nucleic acid construct may be maintained episomally and thus comprises a sequence for autonomous replication, such as an autosomal replication sequence. If the eukaryotic cell is of fungal origin, a suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet, 29:482-489). Alternatively, each nucleic acid construct may be integrated in one or more copies into the genome of the eukaryotic cell. Integration into the cell's genome may occur at random by non-homologous recombination but preferably, the nucleic acid construct may be integrated into the cell's genome by homologous recombination as is well known in the art.

In a preferred embodiment, a eukaryotic microbial cell according to the present invention comprises an enzyme having PEP carboxykinase activity, wherein the enzyme is a heterologous enzyme, preferably the heterologous enzyme is derived from a bacterium, more preferably the enzyme having PEP carboxykinase activity is derived from *Escherichia coli*, *Mannheimia* sp., *Actinobacillus* sp., or *Anaeroblospirillum* sp., more preferably *Mannheimia succiniciproducens*, *Actinobacillus succinogenes*, or *Anaerobiospirillum succiniciproducens*.

In a preferred embodiment a nucleotide sequence encoding an enzyme having PEP carboxykinase activity in the eukaryotic cell according to the present invention is expressed in the cytosol. Surprisingly cytosolic activity of the enzyme resulted in an increased production of a dicarboxylic acid by the eukaryotic cell.

It was found that a nucleotide sequence encoding an enzyme having PEP carboxykinase activity may comprise a peroxisomal or mitochondrial targeting signal, for instance as determined by the method disclosed by Schlüter et al, Nucleic acid Research 2007, Vol 25, D815-D822.

It was found that PEP carboxykinase derived from *Actinobacillus succinogenes* comprises a peroxisomal targeting signal. Surprisingly it was found that when the peroxisomal targeting signal was replaced with the corresponding motif in the PEP carboxykinase derived from *Mannheimia succiniproduces*, peroxisomal targeting was prevented.

Preferably, a eukaryotic cell according to the present invention expresses a nucleotide sequence encoding an enzyme having PEP carboxykinase, wherein the enzyme is a PEP carboxykinase, comprising an amino acid sequence that has at least 50, 55, 60, 65, 70, 75, 80, 85, 90, 95, 97, 98, or 99% sequence identity with the amino acid sequence of SEQ ID NO: 3 and/or SEQ ID NO: 5. Preferably, the PEP carboxykinase comprises SEQ ID NO: 3 and or SEQ ID NO: 5.

In one embodiment it may be preferred that the activity of a native or endogenous or homologous enzyme catalysing the conversion of OAA to PEP in the eukaryotic cell according to the present invention is reduced or is completely knocked out. Knocking out or reducing the activity of an enzyme catalysing the conversion of OAA to PEP are known methods to the skilled man in the art. This may for instance be achieved by mutation, disruption or deletion of the nucleotide sequence encoding the enzyme having PEP carboxykinase activity. A reduced activity of a native PEP carboxykinase is preferred in order to prevent the reverse reaction from OAA to PEP to occur.

A eukaryotic microbial cell according to the present invention, preferably is selected from the group consisting of a yeast and a filamentous fungus. A eukaryotic cell preferably belongs to the genera *Saccharomyces*, *Aspergillus*, *Penicillium*, *Pichia*, *Kluyveromyces*, *Yarrowia*, *Candida*, *Hansenula*, *Humicola*, *Torulaspora*, *Trichosporon*, *Brettanornyces*, *Rhizopus*, *Zygosaccharomyces*, *Pachysolen* or *Yamadazyma*. Preferably, the eukaryotic cell belongs to a species *Saccharomyces cerevisiae*, *Saccharomyces uvarum*, *Saccharomyces bayanus*, *Aspergillus niger*, *Penicillium chrysogenum*, *P. symplissicum*, *Pichia stipidis*, *Kiuyveromyces marxianus*, *K. lactis*, *K. thermotolerans*, *Yarrowia lipolytica*, *Candida sonorensis*, *C. glabrata*, *Hansenula polymorpha*, *Torulaspora delbrueckii*, *Brettanomyces bruxellensis*, *Rhizopus orizae* or *Zygosaccharomyces bailli*.

Preferably, a eukaryotic cell according to the invention is a yeast, preferably *Saccharomyces cerevisiae*, preferably a *Saccharomyces cerevisiae* comprising one or more of the nucleotide sequences selected from SEQ ID NO: 9 and SEQ ID NO: 10. The eukaryotic cell may also be a filamentous fungus, preferably *A. niger*, preferably *A. niger* comprising one or more heterologous nucleotide sequences selected from SEQ ID NO: 7, and SEQ ID NO: 8.

In addition to a nucleotide sequence encoding an enzyme having PEP carboxykinase activity, the eukaryotic cell according to the present invention may be further genetically modified or transformed with nucleotide sequences that encode homologous and/or heterologous enzymes that catalyse reactions in the cell resulting in an increased flux towards malic acid, fumaric acid and/or succinic acid. It may for example be favourable to introduce and/or overexpress nucleotide sequences encoding i) a malate dehydrogenase which catalyses the conversion from OAA to malic acid; ii) a fumarase, which catalyses the conversion of malic acid to fumaric acid; or iii) a fumarate reductase that catalyses the conversion of fumaric acid to succinic acid, depending on the dicarboxylic acid to be produced.

Preferably a eukaryotic cell according to the present invention overexpresses a nucleotide sequence encoding a pyruvate carboxylase (PYC), preferably a pyruvate carboxylase that is active in the cytosol upon expression of the nucleotide sequence, for instance a pyruvate carboxylase comprising an amino acid sequence according to SEQ ID NO: 26. Preferably, an endogenous or homologous pyruvate carboxylase is overexpressed. Surprisingly, it was found that overexpressing an endogenous pyruvate carboxylase resulted in increased succinic acid production levels by the eukaryotic cell according to the present invention comprising a phosphoenolpyruvate carboxykinase as described herein. It was found that the concomitant (over)expression of a pyruvate carboxylase and a phosphoenolpyruvate carboxykinase resulted in surprising increase of succinic acid production levels of at least 1.5 as compared to a eukaryotic cell comprising either pyruvate carboxylase or a phosphoenolpyruvate carboxykinase as described herein.

In another preferred embodiment a cell according to the present invention further comprises nucleotide sequence encoding a malate dehydrogenase (MDH) active in the cytosol upon expression of the nucleotide sequence. A cytosolic MDH may be any suitable homologous or heterologous malate dehydrogenase. Preferably the MDH is a S. cerevisiae MDH, such as MDH3 or MDH1. Preferably, the MDH lacks a peroxisomal or mitochondrial targeting signal in order to localize the enzyme in the cytosol. Alternatively, the MDH is S. cerevisiae MDH2 which has been modified such that it is not inactivated in the presence of glucose and is active in the cytosol. It is known that the transcription of MDH2 is repressed and Mdh2p is degraded upon addition of glucose to glucose-starved cells. Mdh2p deleted for the 12 amino-terminal amino acids is less-susceptible for glucose-induced degradation (Minard and McAlister-Henn, J Biol. Chem. 1992 Aug. 25; 267(24):17458-64). Preferably, a eukaryotic cell according to the present invention comprises a nucleotide sequence encoding a malate dehydrogenase that has at least 70%, preferably at least 75, 80, 85, 90, 92, 94, 95, 96, 97, 98, 99% or 100% sequence identity with the amino acid sequence of SEQ ID NO: 14. Preferably, the activity of malate dehydrogenase is increased by overexpressing the encoding nucleotide sequence by known methods in the art.

Preferably, a eukaryotic cell according to the present invention further comprises a nucleotide sequence encoding an enzyme that catalyses the conversion of malic acid to fumaric acid, which may be a heterologous or homologous enzyme. An enzyme that catalyses the conversion of malic acid to fumaric acid, for instance a fumarase, may be derived from any suitable origin, preferably from microbial origin, for instance a yeast such as Saccharomyces or a filamentous fungus, such Rhizopus oryzee. Preferably, a eukaryotic cell according to the present invention comprises a nucleotide sequence encoding a fumarase that has at least 70%, preferably at least 75, 80, 85, 90, 92, 94, 95, 96, 97, 98, 99% sequence identity with the amino acid sequence of SEQ ID NO: 16, preferably the fumarase comprises SEQ ID NO:16.

Preferably, the enzyme catalysing the conversion of malic acid to fumaric acid is active in the cytosol upon expression of the nucleotide sequence. Cytosolic activity of the enzyme having fumarase activity is preferred for a high productivity of a dicarboxylic acid by the eukaryotic cell. In the invent a nucleotide sequence encoding an enzyme having fumarase activity comprises a peroxisomal or mitochondrial targeting signal (for instance as determined by the method disclosed by Schlüter et al, Nucleic acid Research 2007, Vol 25, D815-D822), it may be preferred to delete said targeting signal to localize an enzyme having fumarase activity in the cytosol. Preferably, a nucleotide sequence encoding an enzyme catalysing the conversion from malic acid to fumaric acid is overexpressed by known methods in the art.

Preferably, the cell according to the present invention is a cell wherein at least one gene encoding alcohol dehydrogenase is not functional. An alcohol dehydrogenase gene that is not functional is used herein to describe a eukaryotic cell, which comprises a reduced alcohol dehydrogenase activity compared to a cell wherein all genes encoding an alcohol dehydrogenase are functional. A gene may become not functional by known methods in the art, for instance by mutation, disruption, or deletion, for instance by the method disclosed by Gueldener et. al. 2002, Nucleic Acids Research, Vol. 30, No. 6, e23. Preferably, the cell is a Saccharomyces cerevisiae, wherein one or more genes adh1 and/or adh2, encoding alcohol dehydrogenase are inactivated.

Preferably, the cell according to the present invention further comprises at least one gene encoding glycerol-3-phosphate dehydrogenase which is not functional. A glycerol-3-phosphate dehydrogenase gene that is not functional is used herein to describe a eukaryotic cell, which comprises a reduced glycerol-3-phosphate dehydrogenase activity, for instance by mutation, disruption, or deletion of the gene encoding glycerol-3-phosphate dehydrogenase, resulting in a decreased formation of glycerol as compared to the wild-type cell.

In another preferred embodiment the recombinant eukaryotic cell according to the present invention comprises at least one gene encoding succinate dehydrogenase that is not functional. A succinate dehydrogenase that is not functional is used herein to describe a eukaryotic cell, which comprises a reduced succinate dehydrogenase activity by mutation, disruption, or deletion, of at least one gene encoding succinate dehydrogenase resulting in a increased formation of succinic acid as compared to the wild-type cell. A eukaryotic cell comprising a gene encoding succinate dehydrogenase that is not functional may for instance be Aspergillus niger, preferably an Aspergillus niger, wherein one or more genes encoding succinate dehydrogenase, such as sdhA and is not functional.

Preferably, a eukaryotic cell according to the present invention comprising any one of the genetic modifications described herein is capable of producing at least 0.3, 0.5, 0.7, g/L succinic acid, preferably at least 1 g/L succinic acid, preferably at least 1.5 preferably at least 2, or 2.5, 4.5 preferably at least 8, 10, 15, or 20 g/L succinic acid but usually below 200 or below 150 g/L.

A preferred eukaryotic cell according to the present invention may be able to grow on any suitable carbon source known in the art and convert it to a desirable dicarboxilic acid as mentioned herein before. The eukaryotic cell may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host organism expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the cell is able to convert a carbon source selected from the group consisting of glucose, fructose, galactose, xylose, arabinose, sucrose, lactose, raffinose and glycerol.

In another aspect, the present invention relates to a process for the preparation of a dicarboxylic acid, comprising fermenting the eukaryotic cell according to the present invention in a suitable fermentation medium and preparing the dicarboxylic acid. It was found advantageous to use a eukaryotic cell as defined herein above in the process for the production of a dicarboxylic acid such as succinic acid, because most eukaryotic cells do not require sterile conditions for propagation and are insensitive to bacteriophage infections. The process according to the present invention may be run under aerobic and anaerobic conditions. Preferably, the process is carried out under anaerobic conditions or under micro-aerophilic or oxygen limited conditions. An anaerobic fermentation process is herein defined as a fermentation process run in the absence of oxygen or in which substantially no oxygen is consumed, preferably less than 5, 2.5 or 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The process for the production of a dicarboxylic acid according to the present invention may be carried out at any suitable pH between 1 and 9. Preferably, the pH in the fermentation broth is between 2 and 7, preferably between 3 and 5. It was found advantageous to be able to carry out the process according to the present invention at low pH, since this prevents bacterial contamination and less alkaline salts are needed for titration to maintain the pH at a desired level in the process for the production of a dicarboxylic acid.

A suitable temperature at which the process according to the present invention may be carried out is between 5 and 60° C., preferably between 10 and 50° C., more preferably between 15 and 35° C., more preferably between 18° C. and 30° C. The skilled man in the art knows the optimal temperatures for fermenting a specific eukaryotic cell.

The dicarboxylic acid that is produced in the process according to the present invention may be succinic acid, fumaric acid or malic acid, preferably succinic acid.

Preferably, the dicarboxylic acid is recovered from the fermentation broth by a suitable method known in the art, for instance by crystallisation, ammonium precipitation or ion exchange technology.

Preferably, the dicarboxylic acid that is prepared in the process according to the present invention is further converted into a pharmaceutical, cosmetic, food, feed, or chemical product. Succinic acid may for instance be further converted into a polymer, such as polybutylene succinate (PBS) or other suitable polymers derived therefrom.

The present invention also relates to a fermentation broth comprising a dicarboxylic acid obtainable by the process according to the present invention.

The invention relates to a process for the production of a dicarboxylic acid wherein a eukaryotic cell is used as dicarboxylic acid producer, whereby phosphoenolpyruvate carboxykinase is used to increase dicarboxylic acid production, preferably wherein the phosphoenolpyruvate carboxykinase is active in the cytosol. Preferably the phosphoenolpyruvate carboxykinase is a heterologous enzyme preferably derived from *Actinobacillus succinogenes* or *Mannheimia succiniciproducens*.

Genetic Modifications

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), *Cold Spring Harbor Laboratory, Cold Spring Harbor Laboratory Press*, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

The following examples are for illustrative purposes only and are not to be construed as limiting the invention.

EXAMPLES

Example 1

Cloning of Phosphoenolpyruvate Carboxykinase from *Actinobacillus succinogenes* and *Mannheimia succiniciproducens* in *Aspergillus niger*

1.1. Expression Constructs

Figure 1:
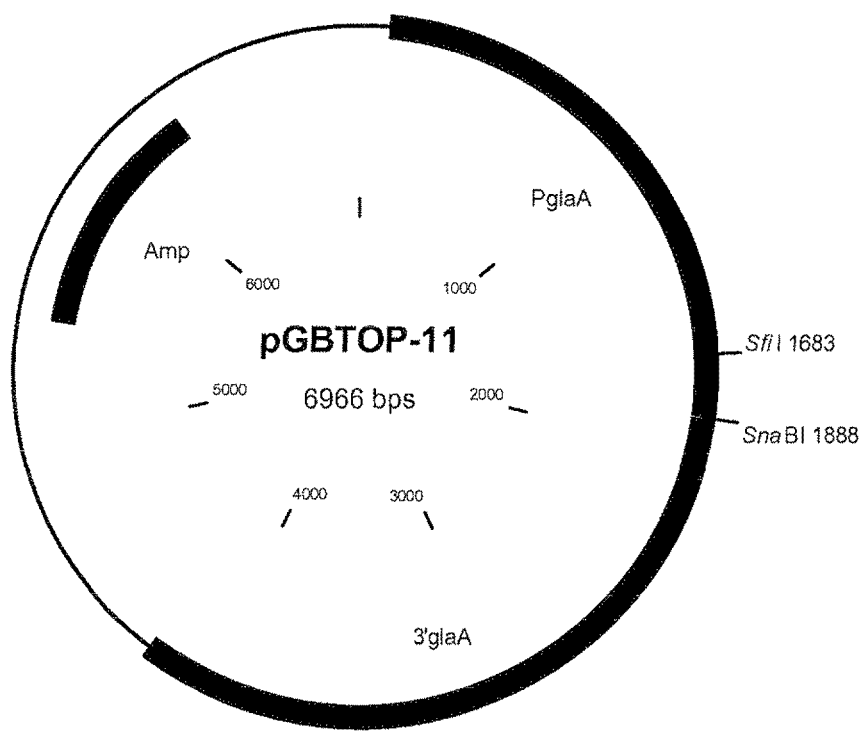
FIG. 1: Map of the pGBTOP-11 vector used for expression of phosphoenolpyruvate carboxykinase in *A. niger*.

Phosphoenolpyruvate carboxykinase [E.C. 4.1.1.49], GenBank accession number 152977907, from *Actinobacillus succinogenes* was analysed for the presence of signal sequences using SignalP 3.0 (http://www.cbs.dtu.dk/services/SignalP/) Bendtsen, J. et al. (2004) Mol. Biol., 340:783-795 and TargetP 1.1 (http://www.cbs.dtu.dk/services/TargetP/) Emanuelsson, O. et al. (2007) Nature Protocols 2, 953-971. Analysis as described by Schlüter et al., (2007) NAR, 35, D815-D822 revealed a putative PTS2 signal sequence at position 115-123. The *A. succinogenes* sequence (amino acid SEQ ID NO: 1, nucleotide sequence SEQ ID NO: 2) was modified to resemble the *Mannheimia succiniciproducens* protein sequence by replacing the amino acids EGY at position 120-122 with DAF (amino acid sequence SEQ ID NO: 3; nucleotide sequence SEQ ID NO: 4). Sequence SEQ ID NO: 3 was subjected to the codon-pair method as disclosed in WO2008/000632 for *A. niger*. The resulting sequence SEQ ID NO: 7 was put behind the constitutive GPDA promoter sequence SEQ ID NO: 11, wherein the last 10 nucleotide sequences were replaced with optimal Kozak sequence CACCGTAAA. Convenient restriction sites were added. The resulting sequence was synthesised at Stoning (Puchheim, Germany). The fragment was SnaBI, SfiI cloned in the *A. niger* expression vector pGBTOP11 (see FIG. 1) using appropriate restriction sites.

Figure 6:
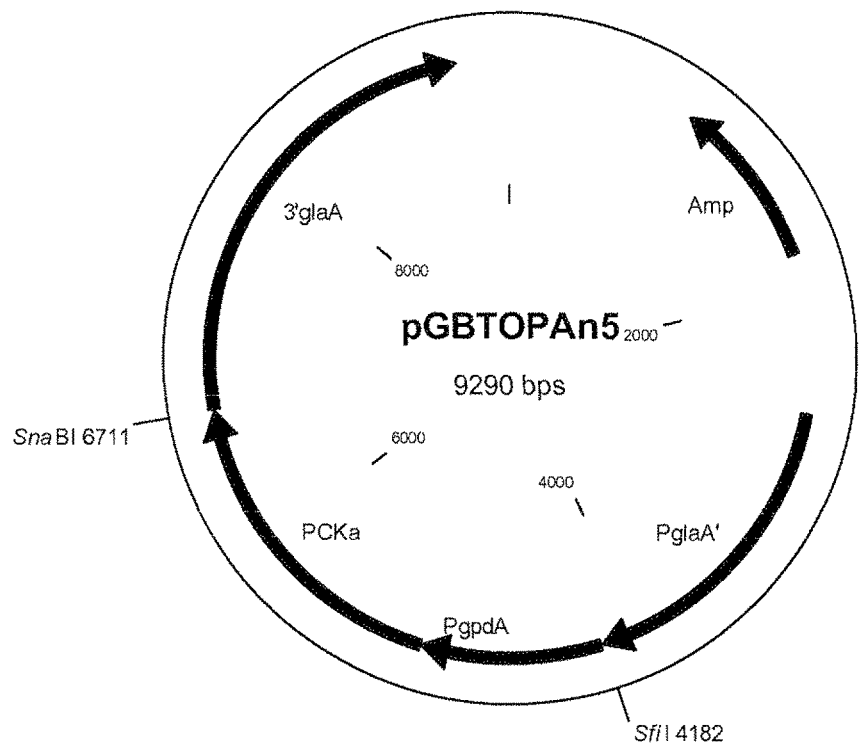
FIG. 6: Map of pGBTOPAn5, wherein the constitutive promoter gpdA drives the expression of PCKa. GlaA flanks were used for integration. *E. coli* DNA was removed by NotI digestion.
Figure 7:
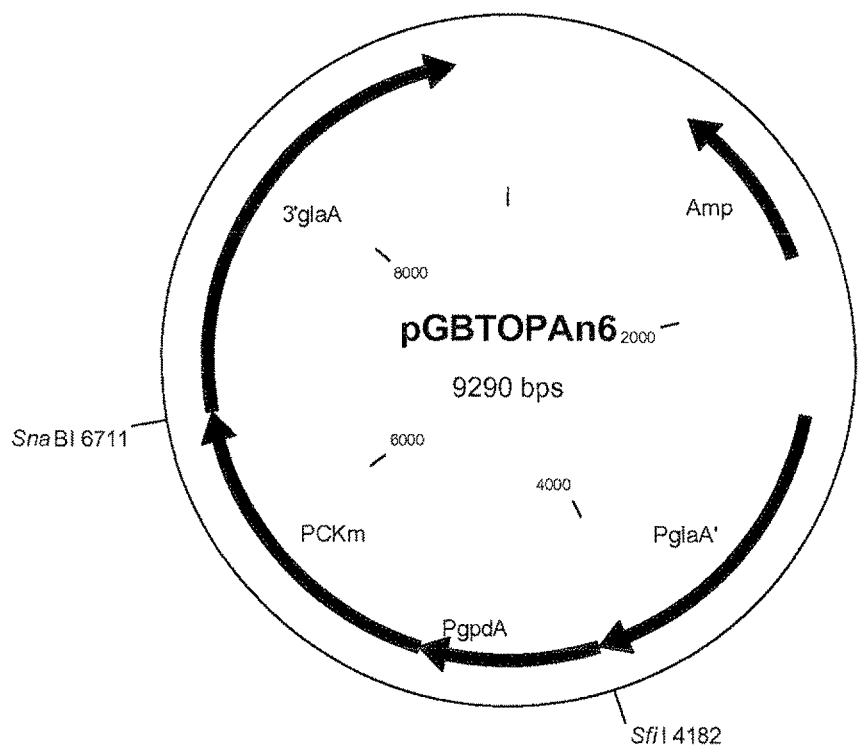
FIG. 7: Map of pGBTOPAn6, wherein the constitutive promoter gpdA drives the expression of PCKm. GlaA flanks were used for integration. *E. coli* DNA was removed by NotI digestion.

Likewise phosphoenolpyruvate carboxykinase [E.C. 4.1.1.49], GenBank accession number 52426348, from *Mannheimia succiniciproducens* was analysed for the presence of signal sequences as described in Schlüter et al., (2007) NAR, 35, D815-D822. The sequence as shown in SEQ ID NO: 5 (nucleotide sequence SEQ ID NO: 6) required no modifications. Subsequently the sequence was subjected to the codon-pair method as disclosed in WO2008/000632 for *A. niger*. The resulting sequence SEQ ID NO: 8 was put behind the constitutive GPDA promoter sequence SEQ ID NO: 11, and convenient restriction sites were added. The resulting sequence was synthesised at Sloning (Puchheim, Germany). The fragment was SnaBI, SfiI cloned in *A. niger* expression vector pGBTOP11 (see FIG. 1) using appropriate restriction sites. After cloning of the PCKa gene into pGBTOP11, the vector was renamed pGBTOPAn5 (FIG. 6). After cloning of the PCKa gene into pGBTOP11, the vector was renamed pGBTOPAn6 (FIG. 7).

1.2. Transformation of *A. niger*

*A. niger* WT-1: This *A. niger* strain is CBS513.88 comprising deletions of the genes encoding glucoamylase (glaA), fungal amylase and acid amylase. *A. niger* WT-1 was constructed by using the "MARKER-GENE FREE" approach as described in EP 0 635 574 B1.

The expression constructs are co-transformed to strain *A. niger* WT-1 according to the method described by Tilburn, J. et al. (1983) Gene 26, 205-221 and Kelly, J. & Hynes, M. (1985) EMBO J., 4, 475-479 with the following modifications:

Spores are germinated and cultivated for 16 hours at 30 degrees Celsius in a shake flask placed in a rotary shaker at 300 rpm in *Aspergillus* minimal medium (100 ml). *Aspergillus* minimal medium contains per liter: 6 g NaNO$_3$, 0.52 g KCl, 1.52 g KH$_2$PO$_4$, 1.12 ml 4 M KOH, 0.52 g MgSO$_4$.7H$_2$O, 10 g glucose, 1 g casaminoacids, 22 mg ZnSO$_4$.7H$_2$O, 11 mg H$_3$BO$_3$, 5 mg FeSO$_4$.7H$_2$O, 1.7 mg CoCl$_2$.6H$_2$O, 1.6 mg CuSO$_4$.5H$_2$O, 5 mg MnCl$_2$.2H$_2$O, 1.5 mg Na$_2$MoO$_4$.2H$_2$O, 50 mg EDTA, 2 mg riboflavin, 2 mg thiamine-HCl, 2 mg nicotinamide, 1 mg pyridoxine-HCL, 0.2 mg panthotenic acid, 4 g biotin, 10 ml Penicillin (5000 IU/ml) Streptomycin (5000 UG/ml) solution (Gibco).

Novozym 234™ (Novo Industries) instead of helicase is used for the preparation of protoplasts;

After protoplast formation (60-90 minutes), KCl buffer (0.8 M KCl, 9.5 mM citric acid, pH 6.2) is added to a final volume of 45 ml, the protoplast suspension is centrifuged for 10 minutes at 3000 rpm at 4 degrees Celsius in a swinging-bucket rotor. The protoplasts are resuspended in 20 ml KC buffer and subsequently 25 ml of SIC buffer (1.2 M sorbitol, 10 mM Tris-HCl pH 7.5, 50 mM CaCl$_2$) is added. The protoplast suspension is centrifuged for 10 minutes at 3000 rpm at 4 degrees Celsius in a swinging-bucket rotor, washed in STC-buffer and resuspended in SIC-buffer at a concentration of 10E8 protoplasts/ml;

To 200 microliter of the protoplast suspension, the DNA fragment, dissolved in 10 microliter TE buffer (10 mM Tris-HCl pH 7.5, 0.1 mM EDTA) and 100 microliter of PEG solution (20% PEG 4000 (Merck), 0.8 M sorbitol, 10 mM Tris-HCl pH 7.5, 50 mM CaCl$_2$) is added;

After incubation of the DNA-protoplast suspension for 10 minutes at room temperature, 1.5 ml PEG solution (60% PEG 4000 (Merck), 10 mM Tris-HCl pH 7.5, 50 mM CaCl$_2$) is added slowly, with repeated mixing of the tubes. After incubation for 20 minutes at room temperature, suspensions are diluted with 5 ml 1.2 M sorbitol, mixed by inversion and centrifuged for 10 minutes at 4000 rpm at room temperature. The protoplasts are resuspended gently in 1 ml 1.2 M sorbitol and plated onto solid selective regeneration medium consisting of either *Aspergillus* minimal medium without riboflavin, thiamine.HCL, nicotinamide, pyridoxine, panthotenic acid, biotin, casaminoacids and glucose. In case of acetamide selection the medium contains 10 mM acetamide as the sole nitrogen source and 1 M sucrose as osmoticum and C-source. Alternatively, protoplasts are plated onto PDA (Potato Dextrose Agar, Oxoid) supplemented with 1-50 microgram/ml phleomycin and 1M sucrose as osmoticum. Regeneration plates are solidified using 2% agar (agar No. 1, Oxoid L11). After incubation for 6-10 days at 30 degrees Celsius, conidiospores of transformants are transferred to plates consisting of *Aspergillus* selective medium (minimal medium containing acetamide as sole nitogen source in the case of acetamide selection or PDA supplemented with 1-50 microgram/ml phleomycin in the case of phleomycin selection) with 2% glucose and 1.5% agarose (Invitrogen) and incubated for 5-10 days at 30 degrees Celsius. Single transformants are isolated and this selective purification step is repeated once upon which purified transformants are stored.

1.3. Shake Flask Growth of *A. niger*

In total 10 transformants are selected for each construct and the presence of the construct is confirmed by PCR using primers specific for the constructs. Subsequently spores are inoculated in 100 ml *Aspergillus* minimal enriched medium comprising 100 g/l glucose. Strains are grown in an incubator at 250 rotations per minute for four days at 34 degrees Celsius. The supernatant of the culture medium is analysed for oxalic acid, malic acid, fumaric acid and succinic acid formation by HPLC and compared to a non transformed strain.

1.4 HPLC Analysis

HPLC is performed for the determination of organic acids and sugars in different kinds of samples. The principle of the separation on a Phenomenex Rezex-RHM-Monosaccharide column is based on size exclusion, ion-exclusion and ion-exchange using reversed phase mechanisms. Detection takes place by differential refractive index and ultra violet detectors.

Example 2A

Cloning of Phosphoenolpyruvate Carboxykinase from *Actinobacillus succinogenes* or *Mannheimia succiniciproducens* in *Saccharomyces cerevisiae*

2A.1. Expression Constructs

Figure 2:
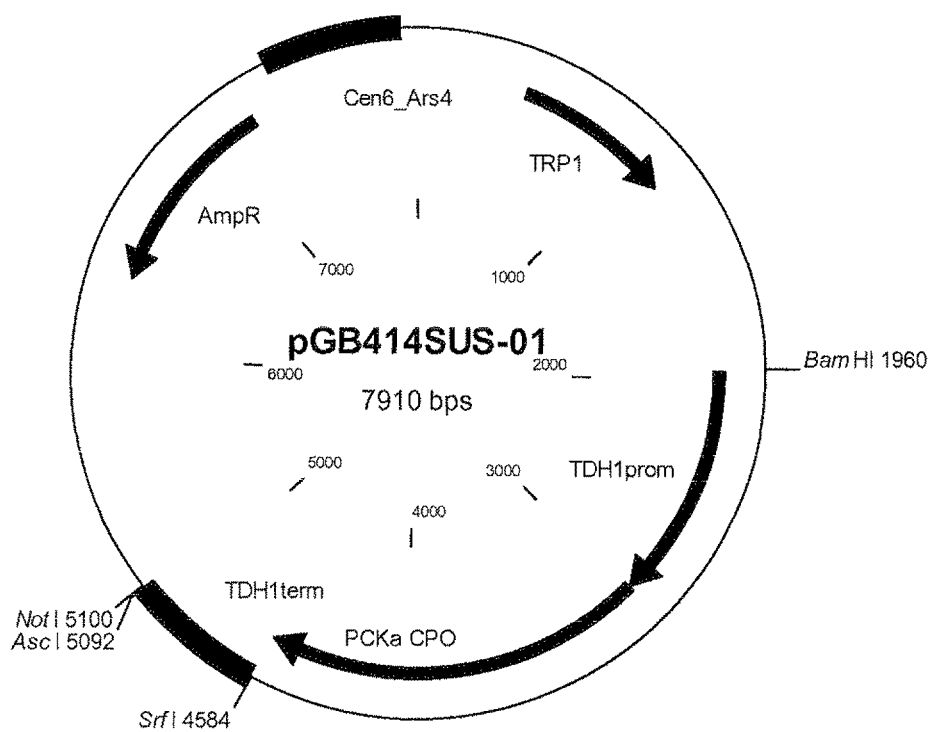
FIG. 2: Plasmid map of pGB414SUS-01, encoding PEP carboxykinase from *Actinobacillus succinogenes* for expression in *Saccharomyces cerevisiae*. CPO denotes codon pair optimized.

Phosphoenolpyruvate carboxykinase [E.C. 4.1.1.49] Gen Bank accession number 152977907 from *Actinobacillus succinogenes* was analysed for the presence of signal sequences as described under §1.1. SEQ ID NO: 3 was subjected to the codon-pair method as disclosed in WO2008/000632 for *S. cerevisiae*. The resulting sequence SEQ ID NO: 9 was put behind the constitutive TDR1 promoter sequence SEQ ID NO: 12 and before the TDH1 terminator sequence SEQ ID NO: 13, and convenient restriction sites were added. The resulting sequence was synthesised at Sloning (Puchheim, Germany). The expression construct pGBS414SUS-01 was created after a BamHI/NotI restriction of the *S. cerevisiae* expression vector pRS414 (Sirkoski R. S, and Hieter P, Genetics, 1989, 122(1):19-27) and subsequently ligating in this vector a BamHI/NotI restriction fragment consisting of the phosphoenolpyruvate carboxykinase (origin *Actinobacillus* succinogenes) synthetic gene construct (FIG. 2). The ligation mix is used for transformation of *E. coli* DH10B (Invitrogen) resulting in the yeast expression construct pGBS414SUS-01 (FIG. 2).

Figure 3:
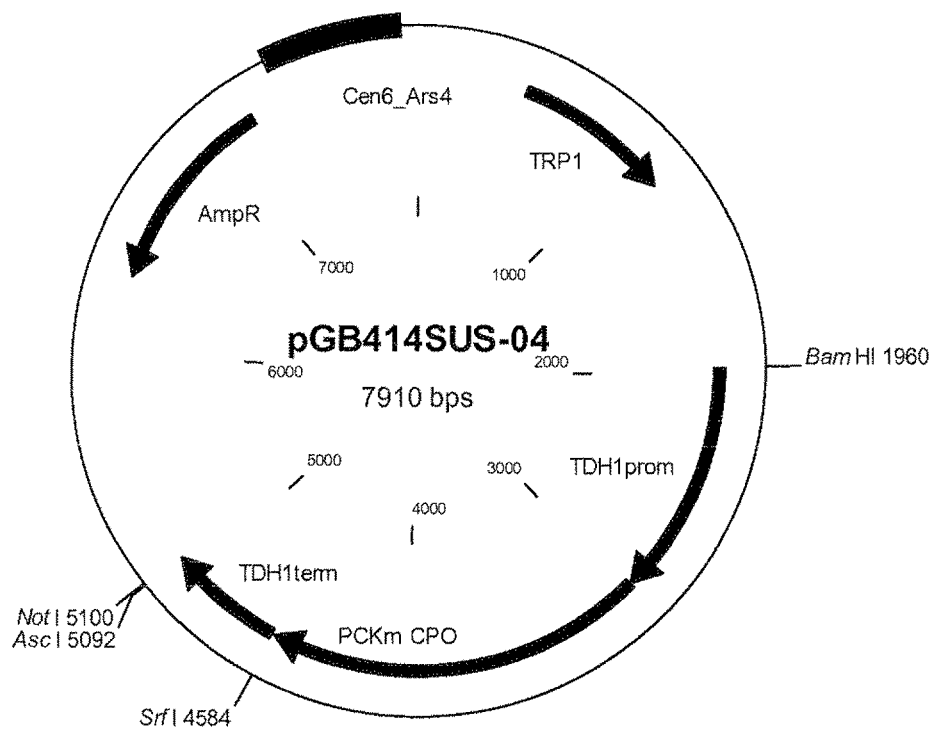
FIG. 3: Plasmid map of pGB414SUS-04, encoding PEP carboxykinase from *Mannheimia succiniciproducens* for expression in *Saccharomyces cerevisiae*. CPO denotes codon pair optimized.

Phosphoenolpyruvate carboxykinase [E.C. 4.1.1.49] GenBank accession number 52426348 from *Mannheimia succiniciproducens* identified and modified as described under §1.1. SEQ ID NO: 5 was subjected to the codon-pair method as disclosed in WO2008/000632 for *S. cerevisiae*. The resulting sequence SEQ ID NO 10 was put behind the constitutive TDH1 promoter sequence SEQ ID NO: 12 and before the TDH1 terminator sequence SEQ ID NO: 13, and convenient restriction sites were added. The resulting sequence was synthesised at Stoning (Puchheim, Germany). The expression construct pGBS414SUS-04 was created after a BamHI/NotI restriction of the *S. cerevisiae* expression vector pRS414 (Sirkoski R. S, and Hieter P, Genetics, 1989, 122(1):19-27) and subsequently ligating in this vector a BamHI/NotI restriction fragment consisting of the phosphoenolpyruvate carboxykinase (origin *Mannheimia succiniciproducens*) synthetic gene construct (FIG. 3). The ligation mix is used for transformation of *E. coli* DH10B (Invitrogen) resulting in the yeast expression construct pGBS414SUS-04 (FIG. 3).

2A.2. Transformation and Shake Flask Growth

The constructs pGBS414SUS-01 and pGBS414SUS-04 are independently transformed into *S. cerevisiae* strains CEN.PK113-6B (MATA ura3-52 leu2-112 trp1-289), RWB066 (MATA ura3-52 leu2-112 trp1-289 adh1::lox adh2::Kanlox) and RWB064 (MATA ura3-52 leu2-112 trp1-289 adh1::lox adh2::lox gpd1::Kanlox). Transformation mixtures are plated on Yeast Nitrogen Base (YNB) w/o AA (Difco)+2% glucose supplemented with appropriate amino acids. Transformants are inoculated in Verduyn medium comprising glucose, supplemented with appropriate amino acids (Verduyn et al., 1992, Yeast. July; 8(7):501-17) and grown under aerobic, anaerobic and oxygen-limited conditions in shake flasks. The medium for anaerobic cultivation is supplemented with 0.01 g/l ergosterol and 0.42 g/l Tween 80 dissolved in ethanol (Andreasen and Stier, 1953, J. cell. Physiol, 41, 23-36; Andreasen and Stier, 1954, J. Cell. Physiol, 43: 271-281). All yeast cultures are grown at 30° C. in a shaking incubator at 250-280 rpm. At different incubation times, aliquots of the cultures are removed, centrifuged and the medium was analysed by HPLC for formation of oxalic acid, malic acid, fumaric acid and succinic acid as described under section 1.4.

Example 2B

Cloning of Phosphoenolpyruvate Carboxykinase from *Actinobacillus succinogenes* or *Mannheimia succiniciproducens* in *Saccharomyces cerevisiae*

2B.1. Expression Constructs

Figure 8:
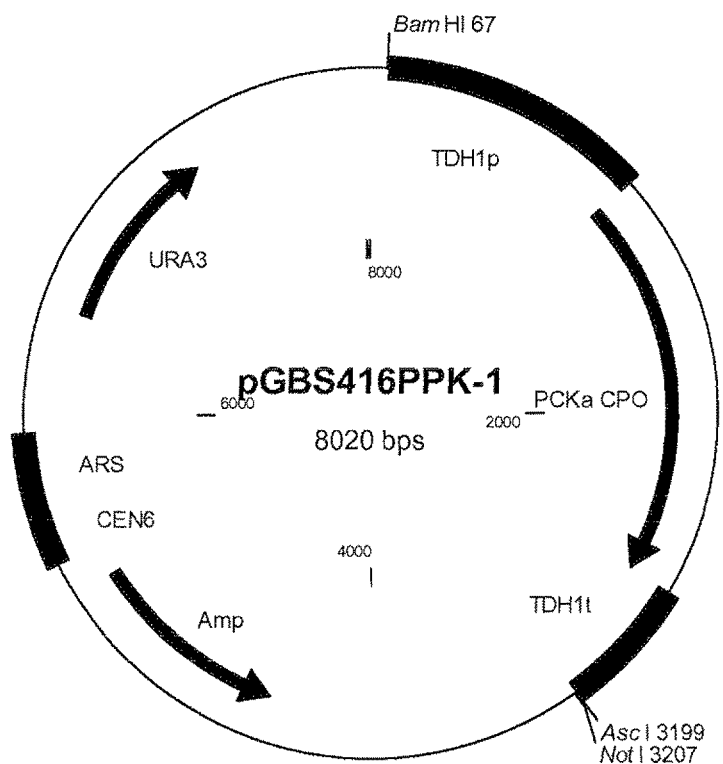
FIG. 8: Plasmid map of pGBS416PPK-1, encoding PEP carboxykinase from *Actinobacillus succinogenes* for expression in *Saccharomyces cerevisiae*. CPO denotes codon pair optimized.

In a similar way as disclosed in Example 2A.1 the PCKa gene (SEQ ID NO: 9) was ligated into *S. cerevisiae* expression vector pRS416 (Sirkoski R. S, and Hieter P, Genetics, 1989, 122(1):19-27). The ligation mix was used for transformation of *E. coli* TOP10 cells (Invitrogen) resulting in the yeast expression construct pGBS416PPK-1 (FIG. 8).

Figure 9:
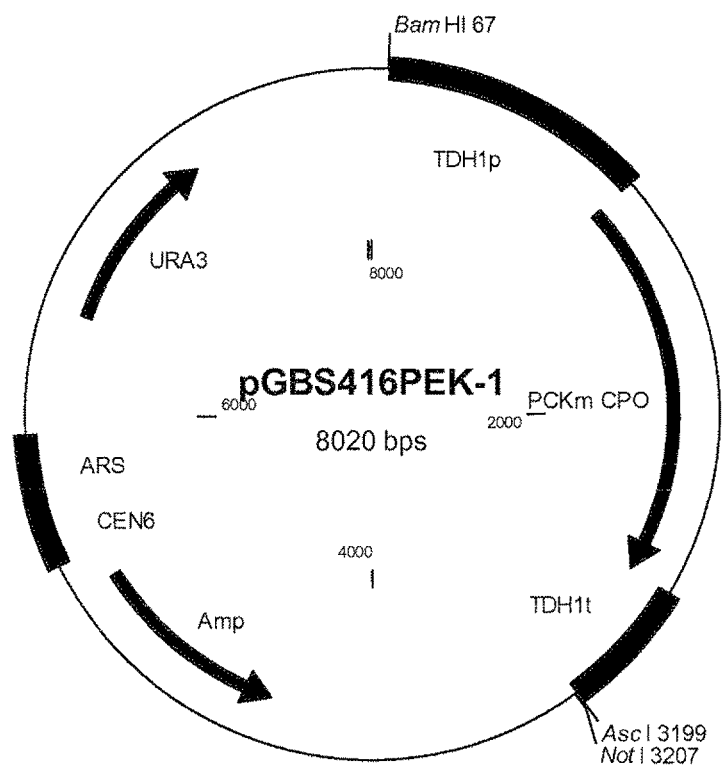
FIG. 9: Plasmid map of pGBS416PEK-1, encoding PEP carboxykinase from *Mannheimia succiniciproducens* for expression in *Saccharomyces cerevisiae*. CPO denotes codon pair optimized.

Likewise, the PCKm gene (SEQ ID NO: 10) was ligated into pRS416. The ligation mix was used for transformation of *E. coli* TOP10 cells (Invitrogen) resulting in the yeast expression construct pGBS416PEK-1 (FIG. 9).

2B.2. Transformation and Microtiterplates (MTP's) Growth Experiments

The constructs pGBS416PPK-1 and pGBS416PEK-1 were independently transformed into *S. cerevisiae* strain CEN.PK113-5D (MA TA ura3-52). As negative control, empty vector pRS416 was transformed into strain CEN.PK113-5D. Transformation mixtures were plated on Yeast Nitrogen Base (YNB) w/o AA (Difco) 4-2% glucose. The following numbers of individual transformants were inoculated in duplo in 250 microliters Verduyn medium comprising 2% glucose in 96 deep-well MTP's and pre-cultured at 30 degrees Celsius, 550 rpm, and a humidity of 80% in an Infors Microplate shaking incubator: 12 pGBS416PPK-1 (PCKa), 12 pGBS416PEK-1 (PCKm) and 24 pRS416 empty vector control transformants. After 3 days, 25 microliters of the pre-culture present in the wells of the MTP's were transferred to new 96 deep-well MTP plates containing Verduyn medium containing glucose and CaCO3 (end-concentrations: glucose 10%, CaCO3 1% w/v in a total volume of 250 microliters). After 7 days of growth at 30 degrees Celsius, 550 rpm, and a humidity of 80% in an Infors Microplate shaking incubator, the MTP's were centrifuged for 2 minutes at 2000 rpm, 200 microliters of supernatant was harvested using the Multimek 96 (Beckman), and the supernatant was analyzed by HPLC as described in Example 1.4 for the presence succinic acid. The results are shown in Table 2.

TABLE 1

Effect of insertion of PCKa and PCKm in *S. cerevisiae* on succinic acid production levels, compared to control strain comprising empty vector pRS416 after 7 days of cultivation.

| S. cerevisiae strain CEN.PK 113-5D, comprising plasmid: | Succinic acid (mg/L) |
|---|---|
| pRS416 | 203 ± 48 (n = 48) |
| pGBS416PPK-1 (PCKa) | 259 ± 63 (n = 24) |
| pGBS416PEK-1 (PCKm) | 268 ± 49 (n = 24) |

The results in Table 1 show that introduction and overexpression of phosphoenolpyruvate carboxykinase from *Actinobacillus succinogenes* or *Mannheimia succiniciproducens* resulted in an increased production level of succinic acid in *S. cerevisiae* (1.28 fold, p=4.92E-, and 1.32 fold, p=2.95E-6 Students t-test, respectively).

Example 2C

Cloning of Phosphoenolpyruvate Carboxykinase from *Actinobacillus succinogenes* or *Mannheimia succiniciproducens*, Malate Dehydrogenase from *Saccharomyces Cerevisiae* and Fumarase from *Rhyzopus oryzae* in *Saccharomyces cerevisiae*

2C.1. Gene Sequences
Phosphoenolpyruvate Carboxykinase:

Gene sequences of PEP carboxykinase from *A. succinogenes* (PCKa) and *M. succiniciproducens* (PCKm) were designed and synthesized as described under 2A.1.

Malate Dehydrogenase:

Peroxisomal malate dehydrogenase (Mdh3) [E.C. 1.1.1.37], GenBank accession number 1431095, was analysed for peroxisomal targeting in filamentous fungi using the PTS1 predictor http://mendel.imp.ac.at/mendeljsp/sat/pts1/PTS1predictor.jsp with the fungi-specific prediction function. The C-terminal amino acids at position 341-343 (SKL) were removed resulting in protein SEQ ID NO: 14. SEQ ID NO: 14 was subjected to the codon-pair method as disclosed in WO2008/000632 for *S. cerevisiae* resulting in SEQ ID NO: 15. The stop codon TGA in SEQ ID NO: 15 was modified to TAAG. The nucleotide sequence SEQ ID NO: 15 containing TAAG as stop codon was synthesized behind the constitutive TDH3 promoter sequence SEQ ID NO: 18 (600 bp upstream of start codon) and before the TDH3 terminator sequence SEQ ID NO: 19 (300 bp downstream of stop codon), and convenient restriction sites were added. The synthetic construct TDH3p-MDH3-TDH3t (SEQ ID NO: 20) was synthesised at Stoning (Puchheim, Germany).

Fumarase:

Fumarase [E.C. 4.2.1.2], GenBank accession number 469103, from *Rhizopus oryzae* was analysed for the presence of signal sequences using SignalP 3.0 (http://www.cbs.dtu.dk/services/SignaP/) Bendtsen, J. et al. (2004) Mol. Biol., 340:783-795 and TargetP 1.1 (http://www.cbs.dtu.dk/services/TargetP/) Emanuelsson, O. et al. (2007) Nature Protocols 2, 953-971. A putative mitochondrial targeting sequence in the first 23 amino acid of the protein was identified. To avoid potential targeting to mitochondria in *S. cerevisiae*, the first 23 amino acids were removed resulting in SEQ ID NO: 16 and a methionine amino acid was reintroduced. SEQ ID NO: 16 was subjected to the codon-pair method as disclosed in WO2008/000632 for *S. cerevisiae* delivering nucleotide sequence SEQ ID NO: 17. The stop codon TAA in SEQ ID NO: 17 was modified to TAAG. SEQ ID NO: 17 containing TAAG as stop codon was synthesized behind the constitutive TDH1 promoter sequence SEQ ID NO: 12 and before the TDH1 terminator sequence SEQ ID NO: 13 and convenient restriction sites were added. The synthetic construct TDH1p-FumR-TDH1t (SEQ ID NO: 21) was synthesised at Sloning (Puchheim, Germany).

2C.2. Construction of Expression Constructs

Figure 10:
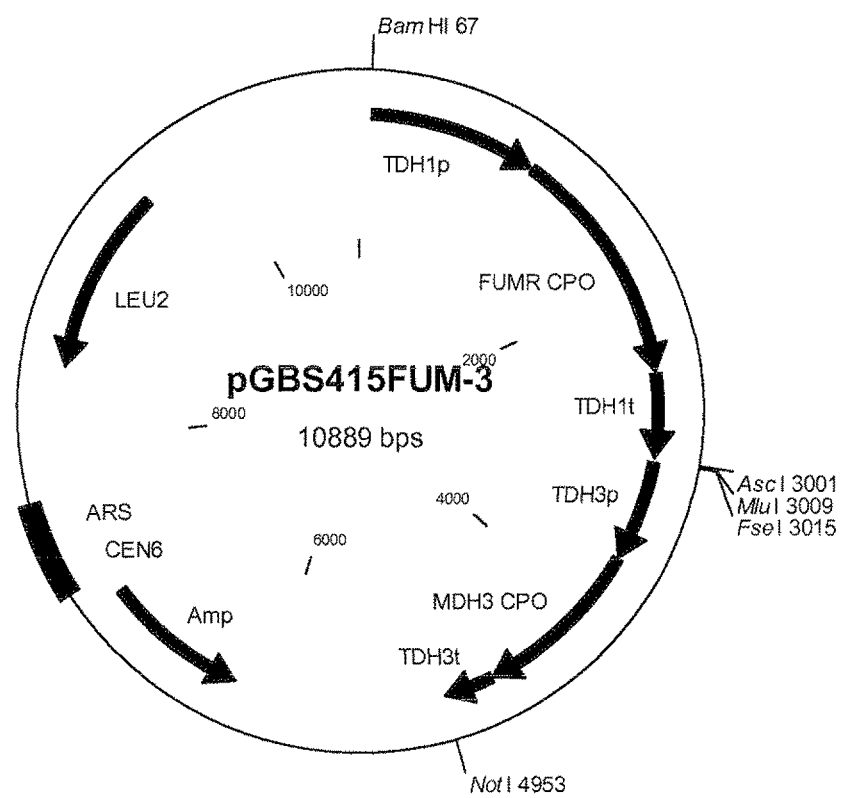
FIG. 10: Plasmid map of pGBS415FUM-3, containing fumarase from *Rhizopus oryzae* (FUMR) and peroxisomal malate dehydrogenase from *Saccharomyces cerevisiae* (MDH3) for expression in *Saccharomyces cerevisiae*. The synthetic gene constructs TDH1 promoter-FUMR-TDH1 terminator and TDH3 promoter-MDH3-TDH3 terminator were cloned into expression vector pRS415. CPO denotes codon pair optimized.

The expression construct pGBS415FUM-3 (FIG. 10) was created after a BamHI/NotI restriction of the *S. cerevisiae* expression vector pRS415 (Sirkoski R. S, and Hieter P, Genetics, 1989, 122(1):19-27) and subsequently ligating in this vector a BamHI/NotI restriction fragment consisting of the fumarase (origin *Rhizopus oryzae*) synthetic gene construct (SEQ ID NO: 21). The ligation mix was used for transformation of *E. coli* TOP10 (Invitrogen) resulting in the yeast expression construct pGBS415FUM-1. Subsequently, pGBK415FUM-1 was restricted with AscI and NotI. To create pGBS415FUM-3, an AscI/NotI restriction fragment consisting of peroxisomal malate dehydrogenase from *S. cerevisiae* (MDH3) synthetic gene construct (SEQ ID NO: 20) was ligated into the restricted pGBS415FUM-1 vector. The ligation mix was used for transformation of *E. coli* TOP10 (Invitrogen) resulting in the yeast expression construct pGBS415FUM-3 (FIG. 10).

Construction of expression constructs pGBS414SUS-01 and pGBS414SUS-04 is described under example 2A.1.

2C.3. *S. cerevisiae* Strains

Plasmids pGBS414SUS-01, pGBS415FUM-3 and pRS416 were transformed into *S. cerevisiae* strain CEN.PK113-6B (MATA ura3-52 leu2-112 trp1-289) to create strain SUC-152. Plasmids pGBS414SUS-04, pGBS415FUM-3 and pRS416 were transformed into *S. cerevisiae* strain CEN.PK113-6B (MATA ura3-52 leu2-112 trp1-289) to create strain SUC-154. A control strain overexpressing only empty vectors (SUC-101) was created by transformation of pRS414, pRS415 and pRS416. All genes were codon pair optimized for expression in *S. cerevisiae*. The expression vectors were transformed into yeast by electroporation. The transformation mixtures were plated on Yeast Nitrogen Base (YNB) w/o AA (Difco)+2% glucose. The genes overexpressed in strains SUC-152 and SUC-154 are described in Table 2.

TABLE 2

Yeast strains constructed for Example 2C.

| Name | Background | Plasmids | Genes |
|---|---|---|---|
| SUC-152 | CEN.PK113-6B | pGBS414SUS-01 | PCKa |
| | | pGBS415FUM-3 | FUMR, MDH3 |
| | | pRS416 (empty vector) | |
| SUC-154 | CEN.PK113-6B | pGBS414SUS-04 | PCKm |
| | | pGBS415FUM-3 | FUMR, MDH3 |
| | | pRS416 (empty vector) | |
| SUC-101 | CEN.PK113-6B | pRS414 (empty vector) | |
| | | pRS415 (empty vector) | |
| | | pRS415 (empty vector) | |

2D.4. Growth Experiments and Succinic Acid and Fumaric Acid Production

Transformants were inoculated in 20 ml pre-culture medium consisting of Verduyn medium (Verduyn et al., 1992, Yeast. July; 8(7):501-17) comprising 2% galactose (w/v) and grown under aerobic conditions in 100 ml shake flasks in a shaking incubator at 30° C. at 250 rpm. After 72 hours, the culture was centrifuged for 5 minutes at 4750 rpm. 1 ml supernatant was used to measure succinic acid levels by HPLC as described in section 1.5. The remaining supernatant was decanted and the pellet (cells) was resuspended in 1 ml production medium. The production medium consisted of Verduyn medium with 10% galactose (w/v) and 1% CaCO3 (w/v). The resuspended cells were inoculated in 50 ml production medium in 100 ml shake flasks and grown in a shaking incubator at 30° C. at 100 rpm. At various time points, 1 ml sample was taken from the culture. Succinic acid and fumaric acid levels were measured by HPLC as described in section 1.4 (FIG. 11).

Figure 11:
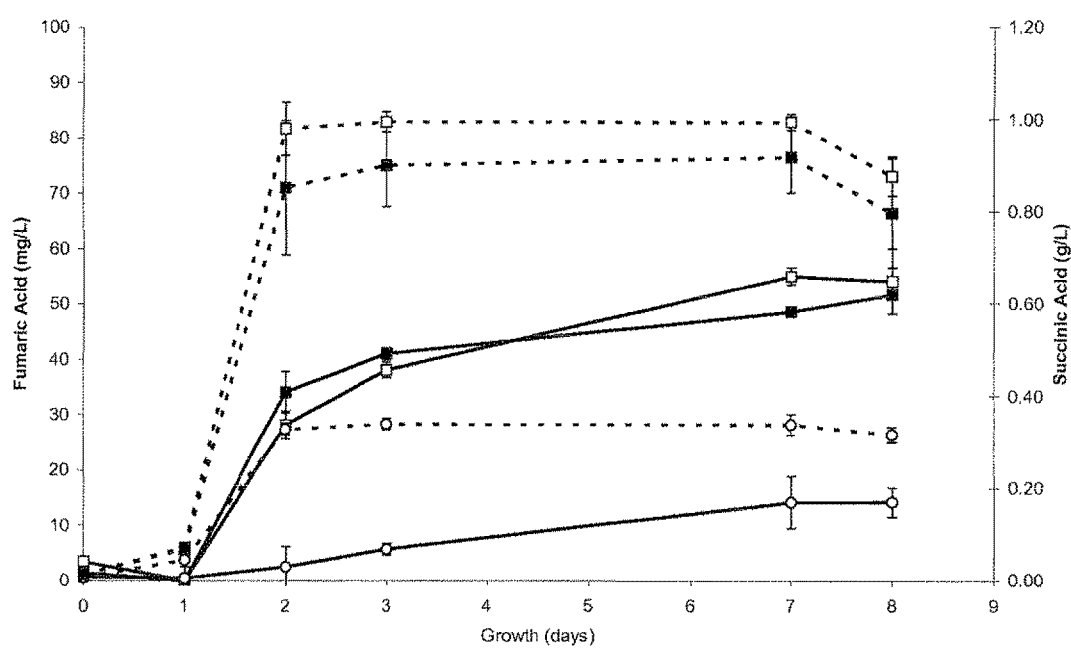
FIG. 11: Succinic (dashed lines) and fumaric acid (solid lines) levels in strains SUC-101 (○, empty vectors control), SUC-152 (□, overexpression of PCKa, MDH3, FUMR), SUC-154 (■, PCKm, MDH3, FUMR). All overexpressed genes were codon pair optimized for expression in *S. cerevisiae*. All data represent averages and standard deviations of 3 independent growth experiments of SUC-152 and 2 independent growth experiments of SUC-154 and averages and standard deviations of 6 independent growth experiments of SUC-101.

Strains transformed with empty vectors (control strain) produced up to 0.3 g/L succinic acid (FIG. 11, dashed line). Overexpression of PEP carboxykinase from *M. succiniciproducens* (PCKm), peroxisomal malate dehydrogenase (MDH3) from *S. cerevisiae* and fumarase from *R. oryzae* (FUMR) resulted in a production level of 0.9 g/L succinic acid. Overexpression of PEP carboxykinase from *A. succinogenes* (PCKa), MDH3 and FUMR resulted in a succinic acid production level of 1.0 g/L. These results show that when *S. cerevisiae* was transformed with a truncated MDH3 and FUMR in addition to either PCKa or PCKm, a further increased amount of succinic acid was produced as compared to a *S. cerevisiae* overexpressing PCKa or PCKm alone (Table 1).

Strains transformed with empty vectors (control strain) produced up to 14 mg/L fumaric acid after 8 days of growth (FIG. 11, solid line). Overexpression of PEP carboxykinase from *A. succinogenes* (PCKa), malate dehydrogenase from *S. cerevisiae* (MDH3) and fumarase from *R. oryzae* (FUMR) resulted in maximal production of 55 mg/L fumaric acid after 7 days of growth. Overexpression of PEP carboxykinase from *M. succiniciproducens* (PCKm), malate dehydrogenase from *S. cerevisiae* (MDH3) and fumarase from *R. oryzae* (FUMR) resulted in maximal production of 52 mg/L fumaric acid after 8 days of growth.

These data show that overexpression of PCKa or PCKm, MDH3 and FUMR in *S. cerevisiae* resulted in increased fumaric acid production levels as compared to a corresponding wild-type *S. cerevisiae*.

Example 2D

Cloning of Phosphoenolpyruvate Carboxykinase from *Actinobacillus succinogenes*, Pyruvate Carboxylase from *Saccharomyces cerevisiae*, Malate Dehydrogenase from *Saccharomyces cerevisiae*, Fumarase from *Rhyzopus oryzae* in *Saccharomyces Cerevisiae* and Fumarate Reductase from *Trypanosoma brucei*

2D.1. Gene Sequences

Glycosomal fumarate reductase (FRDg) [E.C. 1.3.1.6], GenBank accession number 23928422, from *Trypanosoma brucei* was analysed for peroxisomal targeting in filamentous fungi using the PTS1 predictor http://mendel.inp.ac.at/mendeljsp/sat/pts1/predictor.jsp with the fungi-specific prediction function. The C-terminal amino acids at position 1140-1142 (SKI) were removed from the protein, resulting in SEQ ID NO: 22. SEQ ID NO: 22 was subjected to the codon-pair method as disclosed in PCT/EP2007/05594 for expression in *S. cerevisiae*. The resulting sequence SEQ ID NO: 23 was put behind the constitutive TDH3Sc promoter sequence SEQ ID NO: 24 and before the TDH3Sc terminator sequence SEQ ID NO: 25, and convenient restriction sites were added. The stop codon in SEQ ID NO: 23 was modified to TAAG. The resulting sequence was synthesised at Stoning (Puchheim, Germany).

The gene sequence of PEP carboxykinase from *A. succinogenes* was described under 2A.1. Gene sequences of malate dehydrogenase from *S. cerevisiae* and fumarase from *R. oryzae* were described under 2C.1.

Cytoplasmic pyruvate carboxylase from *Saccharomyces cerevisiae* (Pyc2p) [E.C. 6.4.1.1.], GenBank accession number 1041734, SEQ ID NO: 26, is encoded by the nucleotide sequence SEQ ID NO: 27 Genomic DNA from *S. cerevisiae* strain CEN.PK113-5D (MATA ura3-52) was used as template to amplify the PYC2 coding sequence (SEQ ID NO: 29), using primers P1 SEQ ID NO: 28 and P2 SEQ ID NO: 29, and the Phusion DNA polymerase (Finnzymes, Finland) according to manufacturer's instructions. Convenient restriction sites were included in the primers for further cloning purposes.

2D.2. Construction of Expression Constructs

Figure 12:
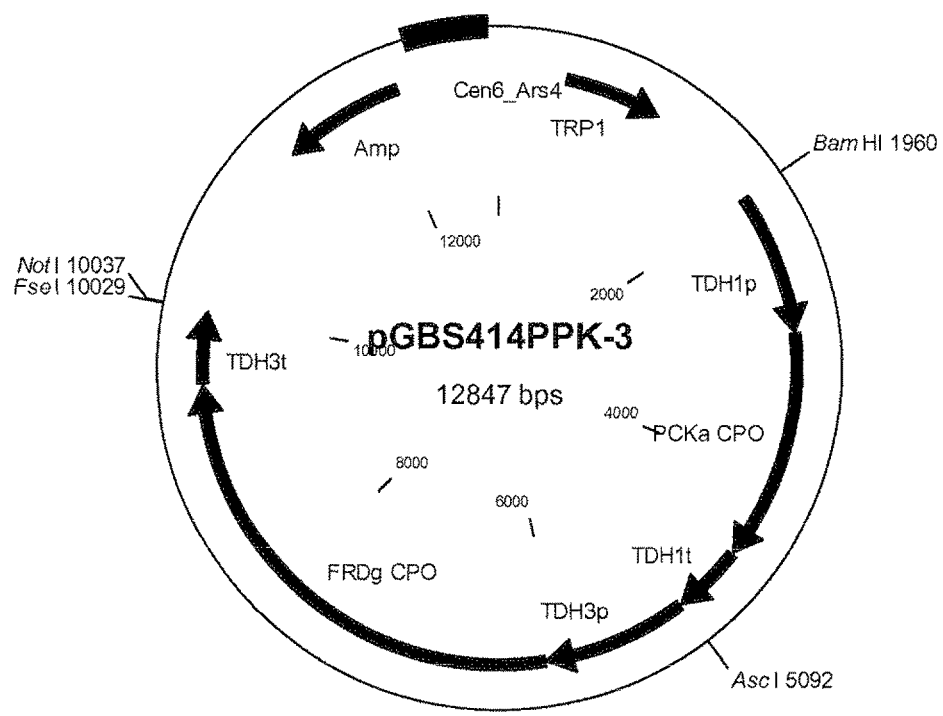
FIG. 12: Plasmid map of pGBS414PPK-3, containing PEP carboxykinase from *Actinobacillus succinogenes* (PCKa) and glycosomal fumarate reductase from *Trypanosoma brucei* (FRDg) for expression in *Saccharomyces cerevisiae*. The synthetic gene constructs TDH1 promoter-PCKa-TDH1 terminator and TDH3 promoter-FRDg-TDH3 terminator were cloned into expression vector pRS414.

The expression construct pGBS414PPK-3 (FIG. 12) was created after a BamHI/NotI restriction of the *S. cerevisiae* expression vector pRS414 (Sirkoski R. S, and Hieter P, Genetics, 1989, 122(1):19-27) and subsequently ligating in this vector a BamHI/NotI restriction fragment consisting of the phosphoenolpyruvate carboxykinase (origin *Actinobacillus succinogenes*) synthetic gene construct (see 2A.1.). The ligation mix was used for transformation of *E. coli* TOP10 (Invitrogen) resulting in the yeast expression construct pGBS414PPK-1. Subsequently, pGBK414PPK-1 was restricted with AscI and NotI. To create pGBS414PPK-3, an AscI/NotI restriction fragment consisting of glycosomal fumarate reductase from *T. brucei* (FRDg) synthetic gene construct (see 2D.1.) was ligated into the restricted pGBS414PPK-1 vector. The ligation mix was used for transformation of *E. coli* TOP10 (Invitrogen) resulting in the yeast expression construct pGBS414PPK-3 (FIG. 12).

Figure 13:
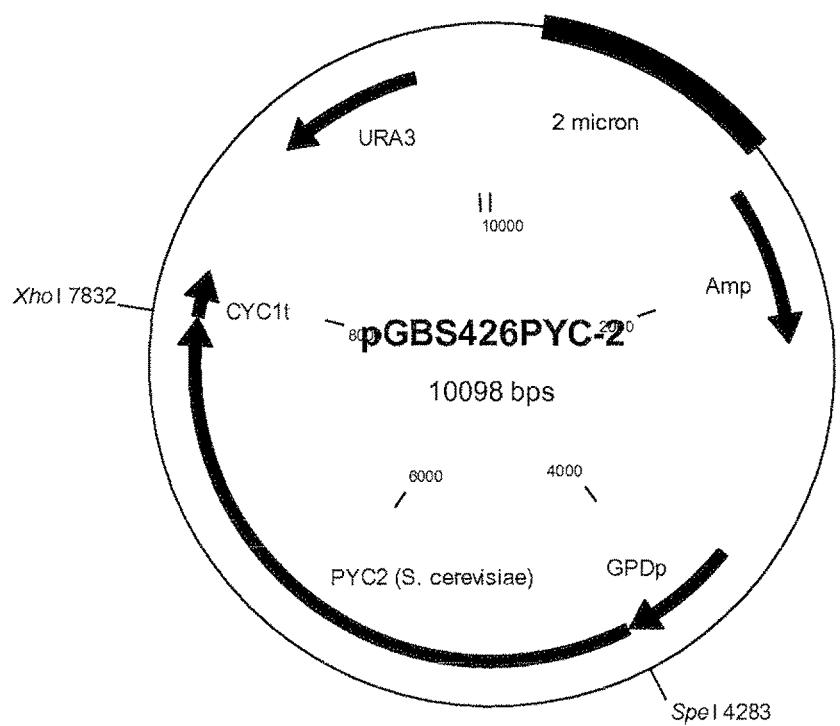
FIG. 13: Plasmid map of pGBS426PYC-2, containing pyruvate carboxylase from *Saccharomyces cerevisiae* for expression in *Saccharomyces cerevisiae*. The PYC2 coding nucleotide sequence was obtained by PCR using genomic DNA from strain CEN.PK113-5D as template and the PCR product was cloned into expression vector p426GPD.

The expression construct pGBS426PYC-2 (FIG. 13) was created after a SpeI/XhoI restriction of the *S. cerevisiae* expression vector p426GPD (Mumberg et al., Gene. 1995 Apr. 14; 156(1):119-22) and subsequently ligating in this vector a SpeI/XhoI restriction fragment consisting of the amplified PYC2 nucleotide sequence (SEQ ID NO: 29). The ligation mix was used for transformation of *E. coli* TOP10 (Invitrogen) resulting in the yeast expression construct pGBS426PYC-2 (FIG. 13).

Figure 14:
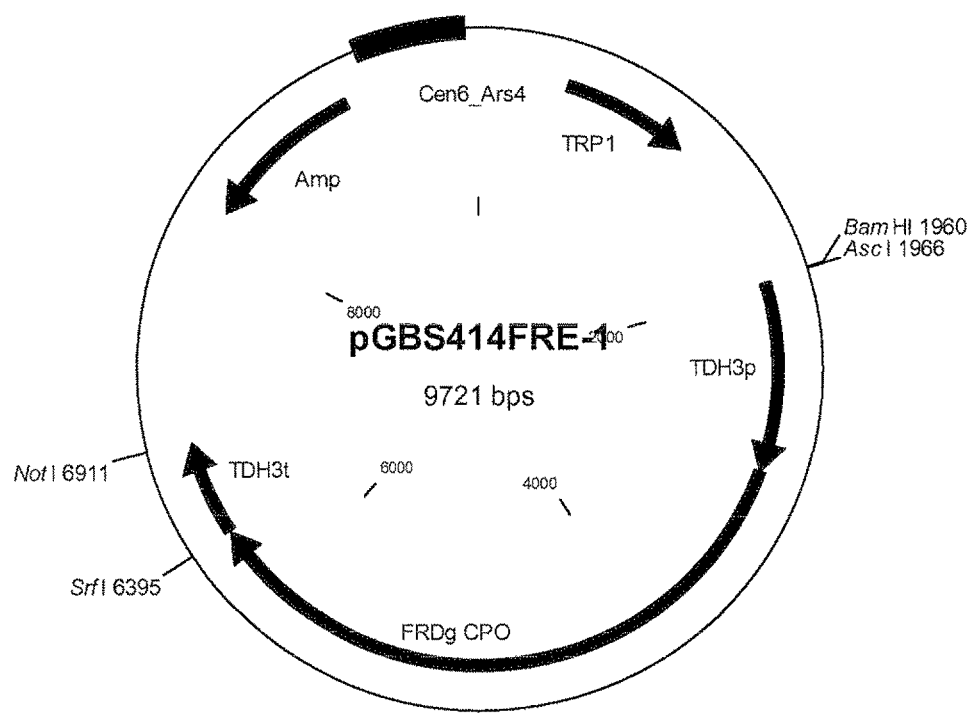
FIG. 14: Plasmid map of pGBS414FRE-1, encoding glycosomal fumarate reductase (FRDg) from Trypanosome brucei for expression in *Saccharomyces cerevisiae*. The synthetic gene construct TDH3 promoter-FRDg-TDH3 terminator was cloned into expression vector pRS414.

Expression construct pGBS414FRE-1 (FIG. 14) was created after a BamHI/NotI restriction of the *S. cerevisiae* expression vector pRS414 (Sirkoski R. S, and Hieter P, Genetics, 1989, 122(1):19-27) and subsequently ligating in this vector a BamHI/NotI restriction fragment consisting of the glycosomal fumarate reductase (origin Trypanosome brucei) synthetic gene construct (see 2D.1.). The ligation mix was used for transformation of *E. coli* TOP10 (Invitrogen) resulting in the yeast expression construct pGBS414FRE-1 (FIG. 14).

Construction of expression construct pGBS415FUM-3 was described under 2C.2.

2D.3. *S. cerevisiae* Strains

Strains SUC-226, SUC-227, SUC-228 and SUC-230 were obtained by transformation of different combinations of the plasmids pGBS414FRE-1, pGBS414PPK-3, pGBS415FUM-1, pGBS426PYC-2 and p426GPD into strain CEN.PK113-6B (MATA ura3-52 leu2-112 trp1-289), as depicted in Table 3.

TABLE 3

Yeast strains constructed for Example 2D.

| Name | Background | Plasmids | Genes |
|------|-----------|----------|-------|
| SUC-226 | CEN.PK113-6B | pGBS414PPK-3 pGBS415FUM-3 p426GPD (empty vector) | PCKa, FRDg FUMR, MDH3 |
| SUC-227 | CEN.PK113-6B | pGBS414PPK-3 pGBS415FUM-3 pGBS426PYC-2 | PCKa, FRDg FUMR, MDH3 PYC2 |
| SUC-228 | CEN.PK113-6B | pGBS414FRE-1 pGBS415FUM-3 pGBS426PYC-2 | FRDg FUMR, MDH3 PYC2 |
| SUC-230 | CEN.PK113-6B | pGBS414FRE-1 pGBS415FUM-3 p426GPD (empty vector) | FRDg FUMR, MDH3 |

2D.4, Growth Experiments and Succinic Acid Production

Growth parameters and sample analysis were performed as described under example 20.4 with the following modifications: pre-culturing was performed using 2% glucose (w/v) as carbon source. In the production medium 10% glucose (w/v) was used as carbon source.

Figure 15:
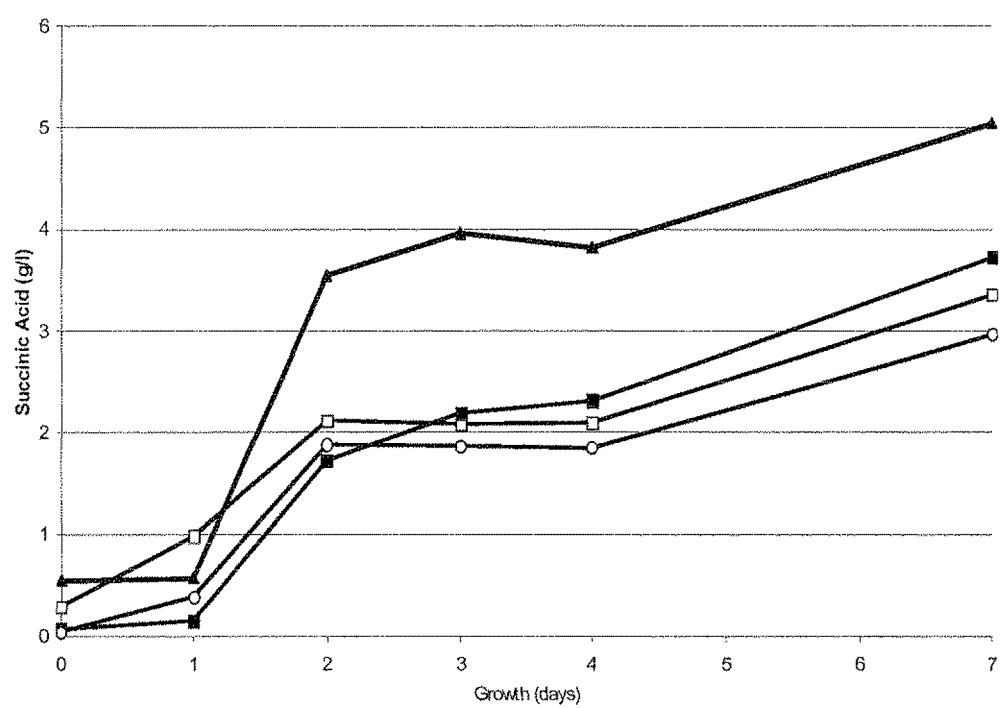
FIG. 15: Succinic acid levels in strains SUC-226 (□, PCKa, MDH3, FUMR, FRDg), -227 (▲, PYC2, PCKa, MDH3, FUMR, FRDg), SUC-228 (■, PYC2, MDH3, FUMR, FRDg) and SUC-230 (○, MDH3, FUMR, FRDg). Data represents the average of 3 independent growth experiments.

As depicted in FIG. 15 strain SUC-230, overexpressing MDH3, FUMR and FRDg, produced up to 3.0 g/L succinic acid. Additional overexpression of PCKa increased succinic acid production up to 3.4 g/L (strain SUC-226), and additional overexpression of PYC2 increased succinic acid production up to 3.7 g/L (strain SUC-228). Surprisingly, overexpression of both PCKa and PYC2 (SUC-227) resulted in 1.5 increase of succinic acid production levels up to 5.0 g/L, as compared to the effect of PCK and PYC alone. These results show a synergistic effect of combined overexpression of both PEP carboxykinase from *A. succinogenes* (PCKa) and pyruvate carboxylase from *S. cerevisiae* (PYC2) on succinic acid production levels in *S. cerevisiae*.

Example 3

Inactivation of Succinate Dehydrogenase Encoding Genes in *Aspergillus niger*

3.1. Identification

Figure 4:
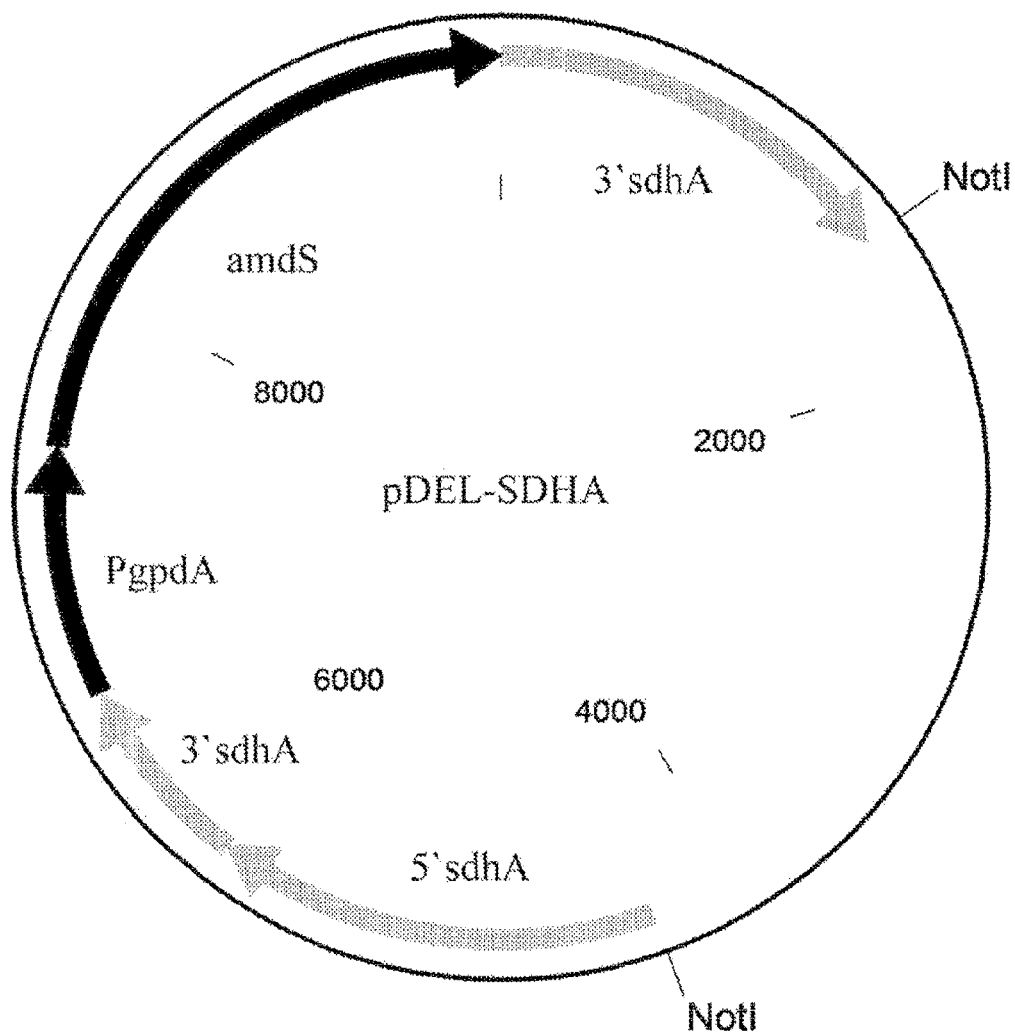
FIG. 4: Plasmid map of pDEL-SDHA.
Figure 5:
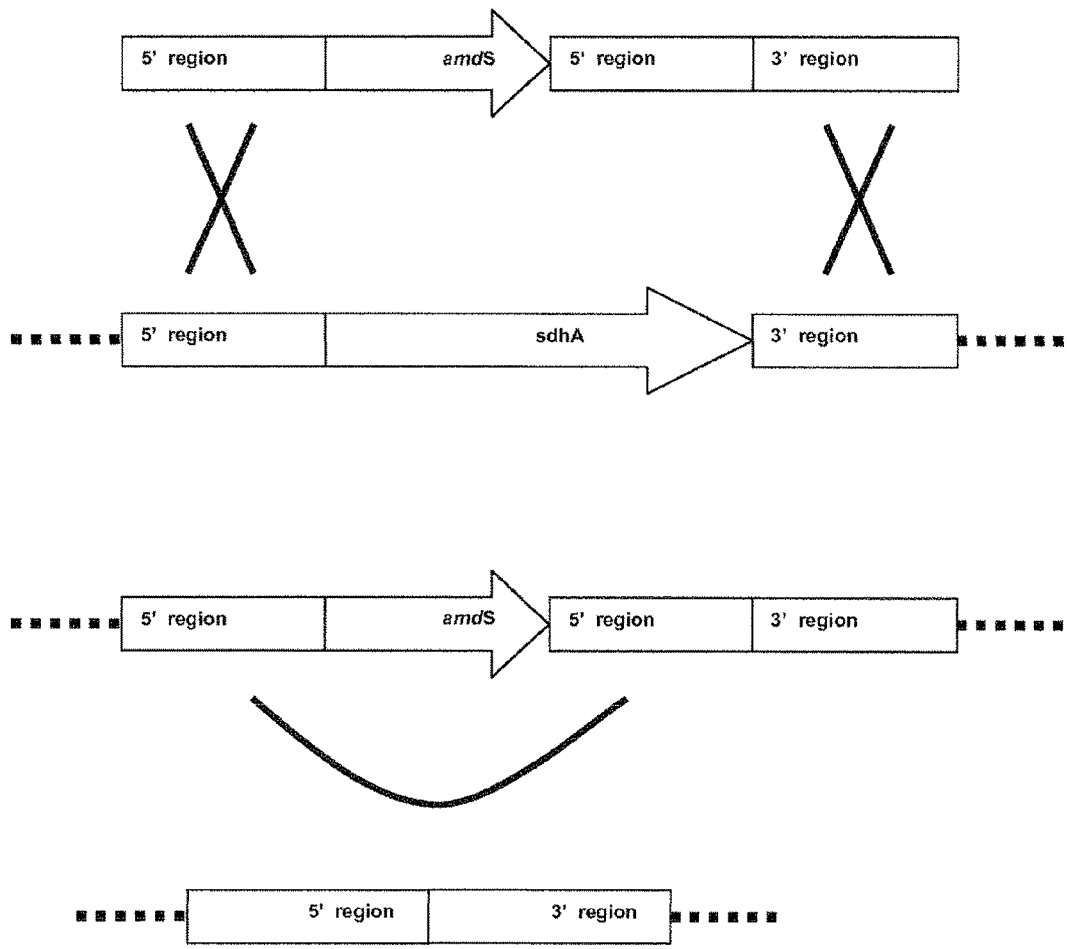
FIG. 5: Replacement scheme of sdhA.

Genomic DNA of *Aspergillus niger* strain CBS513.88 was sequenced and analyzed. Two genes with translated proteins annotated as homologues to succinate dehydrogenase proteins were identified and named sdhA and sdhB respectively. Sequences of the sdhA (An16g07150) and sdhB (An02g12770) loci are available on genbank with accession numbers 145253004 and 145234071, respectively. Gene replacement vectors for sdhA and sdhB were designed according to known principles and constructed according to routine cloning procedures (see FIGS. 4 and 5). The vectors comprise approximately 1000 bp flanking regions of the sdh ORFS for homologous recombination at the predestined genomic loci. In addition, they contain the *A. nidulans* bi-directional amdS selection marker driven by the gpdA promoter, in-between direct repeats. The general design of these deletion vectors were previously described in EP635574B and WO 98/46772.

3.2. Inactivation of the sdhA Gene in *Aspergillus niger*.

Linear DNA of deletion vector pDEL-SDHA (FIG. 4) was isolated and used to transform *Aspergillus niger* CBS513.88 as described in: Biotechnology of Filamentous fungi: Technology and Products. (1992) Reed Publishing (USA); Chapter 6: Transformation p. 113 to 156. This linear DNA can integrate into the genome at the sdhA locus, thus substituting the sdhA gene by the amdS gene as depicted in FIG. 6. Transformants were selected on acetamide media and colony purified according to standard procedures as described in EP635574B. Spores were plated on fluoro-acetamide media to select strains, which lost the amdS marker. Growing colonies were diagnosed by PCR for integration at the sdhA locus and candidate strains tested by Southern analyses for deletion of the sdhA gene. Deletion of the sdhA gene was detectable by the ~2.2 kb size reduction of DNA fragments (4.6 kb wild-type fragment versus 2.4 kb for a successful deletion of SDHA) covering the entire locus and hybridized to appropriate probes. Approximately 9 strains showed a removal of the genomic sdhA gene from a pool of approximately 96 initial transformants.

Strain dSDHA was selected as a representative strain with an inactivated sdhA gene. The production of succinic acid by the dSDHA strain was measured as described in Example 4.

Example 4

Cloning of PCKa and PCKm in *A. niger* dSDHA and Growth in Microtiter Plates (MTP's)

*A. niger* strain dSDHA of example 3.2. was transformed with the expression construct pGBTOPAn5 (FIG. 6) comprising PEP carboxykinase from *Actinobacillus succinigenes* (PCKa, SEQ ID NO: 7) and expression construct pGBTOPAn6 (FIG. 7) comprising PEP carboxykinase from *Mannheimia succinicproducens* (PCKm, SEQ ID NO: 8) as described in Example 1.1., according to the transformation method as described in Example 1.2.

*A. niger* transformants were picked using Qpix and transferred onto MTP's containing selective media. After 7 days of incubation at 30 degrees Celsius the biomass was transferred to MTP's containing PDA by hand or colony picker. After 7 days incubation at 30 degrees Celsius, the biomass was sporulated. These spores were resuspended using the Multimek 96 (Beckman) in 100 microliters minimal enriched *Aspergillus* medium containing 10% glucose. Subsequently 2 MTP's with 170 microliters minimal enriched *Aspergillus* medium containing 10% glucose and 1% CaCO3 were inoculated with 30 microliters of the spore suspension. Likewise dSDHA and control *A. niger* strain CBS513.88 were inoculated in the MTP's. These MTP's were incubated for 5 days at 34 degrees Celsius, 550 rpm at 80% humidity. After 5 days 160 microliters were harvested using the Multimek 96 (Beckman). Succinic acid in the media was measured by HPLC as described in Example 1.4. The results are shown in Table 3.

TABLE 4

Effect of deletion of succinate dehydrogenase (SDHA) and insertion of PCKa and PCKm in *A. niger* on succinic acid production levels

| *A. niger* strain | Succinic acid mg/l |
|-------------------|-------------------|
| CBS513.88 | 38 |
| dSDHA | 50 |
| dSDHA, + PCKa | 160 |
| d,SDHA, + PCKm | 241 |

The results in Table 4 show that insertion of phosphoenol pyruvate carboykinase from both *A. succinogenes* or from *M. succiniciproducens* increased succinic acid production levels by *A. niger*.

The invention claimed is:

1. A recombinant eukaryotic microbial cell comprising a nucleotide sequence encoding a phosphoenolpyruvate carboxykinase enzyme, wherein the phosphoenolpyruvate carboxykinase enzyme comprises an amino acid sequence which has at least 70% sequence identity with the amino acid sequence of SEQ ID NO:3 and/or SEQ ID NO:5, wherein the nucleotide sequence is expressed in the cytosol and the enzyme is active in the cytosol, wherein said recombinant eukaryotic microbial cell is capable of producing an increased amount of a dicarboxylic acid as compared to a wild-type eukaryotic microbial cell, and wherein said recombinant eukaryotic microbial cell is a yeast or a filamentous fungus.

2. The cell according to claim 1, wherein the enzyme is a heterologous enzyme.

3. The cell according to claim 1, wherein the cell overexpresses a nucleotide sequence encoding a pyruvate carboxylase.

4. The cell according to claim 1, wherein the cell further comprises a nucleotide sequence encoding a malate dehydrogenase, wherein the malate dehydrogenase is active in the cytosol upon expression of the nucleotide sequence encoding malate dehydrogenase.

5. The cell according to claim 1, wherein the cell further comprises a nucleotide sequence encoding an enzyme that catalyses the conversion of malic acid to fumaric acid in the cytosol, upon expression of the nucleotide sequence encoding an enzyme that catalyses the conversion of malic acid to fumaric acid.

6. The cell according to claim 1, wherein at least one gene encoding succinate dehydrogenase is not functional.

7. The cell according to claim 1, which is an *Aspergillus niger* comprising a nucleotide sequence encoding a phosphoenolpyruvate carboxykinase of SEQ ID NO:7 and/or SEQ ID NO:8.

8. The cell according to claim 1, which is a *Saccharomyces cerevisiae* comprising a nucleotide sequence encoding a phosphoenolpyruvate carboxykinase of SEQ ID NO:9 and/or SEQ ID NO:10.

9. A process for the preparation of a dicarboxylic acid, comprising fermenting the eukaryotic microbial cell according to claim 1, in a suitable fermentation medium, and preparing the dicarboxylic acid.

10. The process according to claim 9, wherein the dicarboxylic acid is succinic acid, fumaric acid or malic acid.

11. The process according to claim 9, wherein the dicarboxylic acid is further converted into a pharmaceutical, cosmetic, food, feed, or chemical product.

12. The cell according to claim 2, wherein the heterologous enzyme is isolated from a bacterium.

13. The cell according to claim 1, wherein the cell is a *Saccharomyces cerevisiae* cell, or an *Aspergillus niger* cell.

14. The cell according to claim 1, wherein the cell overexpresses a nucleotide sequence encoding a fumarate reductase.

15. The cell according to claim 1, wherein the dicarboxylic acid is succinic acid, fumaric acid, or malic acid.

\* \* \* \* \*

SEQUENCE LISTING

<160> NUMBER OF SEQ ID NOS: 29

<210> SEQ ID NO 1
<211> LENGTH: 538
<212> TYPE: PRT
<213> ORGANISM: Actinobacillus succinogenes

<400> SEQUENCE: 1

```
Met Thr Asp Leu Asn Lys Leu Val Lys Glu Leu Asn Asp Leu Gly Leu
 1               5                  10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
           100                 105                 110

Gly Lys Arg Leu Phe Val Val Glu Gly Tyr Cys Gly Ala Ser Glu Lys
       115                 120                 125

His Arg Ile Gly Val Arg Met Val Thr Glu Val Ala Trp Gln Ala His
   130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
           180                 185                 190

Ile Thr Glu Gly Ile Gln Leu Ile Gly Gly Thr Trp Tyr Gly Gly Glu
       195                 200                 205

Met Lys Lys Gly Met Phe Ser Met Met Asn Tyr Phe Leu Pro Leu Lys
   210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
           260                 265                 270

Glu Ser Gly Val Phe Asn Phe Glu Gly Gly Cys Tyr Ala Lys Thr Ile
       275                 280                 285

Asn Leu Ser Gln Glu Asn Glu Pro Asp Ile Tyr Gly Ala Ile Arg Arg
   290                 295                 300

Asp Ala Leu Leu Glu Asn Val Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
           340                 345                 350

Thr Lys Val Ile Phe Leu Thr Ala Asp Ala Phe Gly Val Leu Pro Pro
       355                 360                 365
```

```
Val Ser Lys Leu Thr Pro Glu Gln Thr Glu Tyr Tyr Phe Leu Ser Gly
    370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
                420                 425                 430

Glu Ala Tyr Leu Val Asn Thr Gly Trp Asn Gly Thr Gly Lys Arg Ile
            435                 440                 445

Ser Ile Lys Asp Thr Arg Gly Ile Ile Asp Ala Ile Leu Asp Gly Ser
450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
                500                 505                 510

Asn Arg Phe Val Lys Asn Phe Val Lys Tyr Thr Ala Asn Pro Glu Ala
            515                 520                 525

Ala Lys Leu Val Gly Ala Gly Pro Lys Ala
530                 535

<210> SEQ ID NO 2
<211> LENGTH: 1617
<212> TYPE: DNA
<213> ORGANISM: Actinobacillus succinogenes

<400> SEQUENCE: 2
atgactgact taaacaaact cgttaaagaa cttaatgact tagggcttac cgatgttaag      60
gaaattgtgt ataacccgag ttatgaacaa cttttcgagg aagaaaccaa accgggtttg     120
gagggtttcg ataaagggac gttaaccacg cttggcgcgg ttgccgtcga tacggggatt     180
tttaccggtc gttcaccgaa agataaatat atcgtttgcg atgaaactac gaaagacacc     240
gtttggtgga acagcgaagc ggcgaaaaac gataacaaac cgatgacgca agaaacttgg     300
aaaagtttga gagaattagt ggcgaaacaa cttccggta  acgtttatt cgtggtagaa     360 ggttactgcg gcgccagtga aaacaccgt  atcggtgtgc gtatggttac tgaagtggca     420
tggcaggcgc attttgtgaa aaacatgttt atccgaccga ccgatgaaga gttgaaaaat     480
ttcaaagcgg attttaccgt gttaaacggt gctaaatgta ctaatccgaa ctggaaagaa     540
caaggtttga cagtgaaaa  ctttgtcgct ttcaatatta ccgaaggtat tcagcttatc     600
ggcggtactt ggtacggcgg tgaaatgaaa aaggtatgt  tctcaatgat gaactacttc     660
ctgccgttaa aggtgtggc  ttccatgcac tgttccgcca acgtaggtaa agacggtgac     720
gtggctattt tcttcggttt atccggtacg ggtaaaacaa cgctttcgac cgatcctaaa     780
cgccaattaa tcggtgatga cgaacacggt tgggatgaat ccggcgtatt taactttgaa     840
ggcggttgtt acgcgaaaac cattaactta tctcaagaaa acgaaccgga tatttacggc     900
gcaatccgtc gtgacgcatt attagaaaac gtcgtggttc gtgcagacgg ttccgttgac     960
tttgacgacg gttcaaaaac agaaaatacc cgtgtttcat atccgattta ccacatcgac    1020
aacatcgttc gtccggtatc gaaagccggt catgcaacca agtgattttt cttaaccgcg    1080
gacgcattcg gcgtattgcc gccggtttca aaactgactc cggaacaaac cgaatactac    1140
```

```
ttcttatccg gctttactgc aaaattagcg ggtacggaac gcggcgtaac cgaaccgact   1200
ccgacattct cggcctgttt cggtgcggca ttcttaagcc tgcatccgat tcaatatgcg   1260
gacgtgttgg tcgaacgcat gaaagcctcc ggtgcggaag cttatttggt gaacaccggt   1320
tggaacggca cgggtaaacg tatttcaatc aaagataccc gcggtattat cgatgcgatt   1380
ttggacggtt caatcgaaaa agcggaaatg ggcgaattgc caatctttaa tttagcgatt   1440
cctaaagcat taccgggtgt tgatcctgct attttggatc cgcgcgatac ttacgcagac   1500
aaagcgcaat ggcaagttaa agcggaagat ttggcaaacc gtttcgtgaa aaactttgtg   1560
aaatatacgg cgaatccgga agcggctaaa ttagttggcg ccggtccaaa agcataa     1617
```

<210> SEQ ID NO 3
<211> LENGTH: 538
<212> TYPE: PRT
<213> ORGANISM: Artificial sequence
<220> FEATURE:
<223> OTHER INFORMATION: PEPCK A.s. wherein EGY is replaced with DAF

<400> SEQUENCE: 3

```
Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110

Gly Lys Arg Leu Phe Val Val Asp Ala Phe Cys Gly Ala Ser Glu Lys
        115                 120                 125

His Arg Ile Gly Val Arg Met Val Thr Glu Val Ala Trp Gln Ala His
    130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
    210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Glu Ser Gly Val Phe Asn Phe Glu Gly Gly Cys Tyr Ala Lys Thr Ile
        275                 280                 285
```

```
Asn Leu Ser Gln Glu Asn Glu Pro Asp Ile Tyr Gly Ala Ile Arg Arg
        290                 295                 300

Asp Ala Leu Leu Glu Asn Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
                340                 345                 350

Thr Lys Val Ile Phe Leu Thr Ala Asp Ala Phe Gly Val Leu Pro Pro
            355                 360                 365

Val Ser Lys Leu Thr Pro Glu Gln Thr Glu Tyr Tyr Phe Leu Ser Gly
370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
                420                 425                 430

Glu Ala Tyr Leu Val Asn Thr Gly Trp Asn Gly Thr Gly Lys Arg Ile
            435                 440                 445

Ser Ile Lys Asp Thr Arg Gly Ile Ile Asp Ala Ile Leu Asp Gly Ser
450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
                500                 505                 510

Asn Arg Phe Val Lys Asn Phe Val Lys Tyr Thr Ala Asn Pro Glu Ala
            515                 520                 525

Ala Lys Leu Val Gly Ala Gly Pro Lys Ala
530                 535

<210> SEQ ID NO 4
<211> LENGTH: 1617
<212> TYPE: DNA
<213> ORGANISM: Artificial sequence
<220> FEATURE:
<223> OTHER INFORMATION: nt PEPCK A.s. EGY replaced with DAF

<400> SEQUENCE: 4
atgactgact taaacaaact cgttaaagaa cttaatgact tagggcttac cgatgttaag     60
gaaattgtgt ataacccgag ttatgaacaa cttttcgagg aagaaaccaa accgggtttg    120
gagggtttcg ataaagggac gttaaccacg cttggcgcgg ttgccgtcga tacggggatt    180
tttaccggtc gttcaccgaa agataaatat atcgtttgcg atgaaactac gaaagacacc    240
gtttggtgga acagcgaagc ggcgaaaaac gataacaaac cgatgacgca gaaacttgg    300 aaaagtttga gagaattagt ggcgaaacaa cttttccggta acgttttatt cgtggtagac    360
gcattctgcg gcgccagtga aaacaccgt atcggtgtgc gtatggttac tgaagtggca    420
tggcaggcgc attttgtgaa aaacatgttt atccgaccga ccgatgaaga gttgaaaaat    480
ttcaaagcgg attttaccgt gttaaacggt gctaaatgta ctaatccgaa ctggaaagaa    540
caaggtttga acagtgaaaa ctttgtcgct ttcaatatta ccgaaggtat tcagcttatc    600
```

-continued

```
ggcggtactt ggtacggcgg tgaaatgaaa aaaggtatgt tctcaatgat gaactacttc    660
ctgccgttaa aaggtgtggc ttccatgcac tgttccgcca acgtaggtaa agacggtgac    720
gtggctattt tcttcggttt atccggtacg ggtaaaacaa cgctttcgac cgatcctaaa    780
cgccaattaa tcggtgatga cgaacacggt tgggatgaat ccggcgtatt taactttgaa    840
ggcggttgtt acgcgaaaac cattaactta tctcaagaaa acgaaccgga tatttacggc    900
gcaatccgtc gtgacgcatt attagaaaac gtcgtggttc gtgcagacgg ttccgttgac    960
tttgacgacg gttcaaaaac agaaaatacc cgtgtttcat atccgattta ccacatcgac   1020
aacatcgttc gtccggtatc gaaagccggt catgcaacca agtgattttt cttaaccgcg   1080
gacgcattcg gcgtattgcc gccggtttca aaactgactc cggaacaaac cgaatactac   1140
ttcttatccg gctttactgc aaaattagcg ggtacggaac gcggcgtaac cgaaccgact   1200
ccgacattct cggcctgttt cggtgcggca ttcttaagcc tgcatccgat tcaatatgcg   1260
gacgtgttgg tcgaacgcat gaaagcctcc ggtgcggaag cttatttggt gaacaccggt   1320
tggaacggca cgggtaaacg tatttcaatc aaagataccc gcgtattat cgatgcgatt   1380
ttggacggtt caatcgaaaa agcggaaatg ggcgaattgc caatctttaa tttagcgatt   1440
cctaaagcat taccgggtgt tgatcctgct attttggatc cgcgcgatac ttacgcagac   1500
aaagcgcaat ggcaagttaa agcggaagat ttggcaaacc gtttcgtgaa aaactttgtg   1560
aaatatacgg cgaatccgga agcggctaaa ttagttggcg ccggtccaaa agcataa      1617
```

<210> SEQ ID NO 5
<211> LENGTH: 538
<212> TYPE: PRT
<213> ORGANISM: Mannheimia succiniciproducens

<400> SEQUENCE: 5

```
Met Thr Asp Leu Asn Gln Leu Thr Gln Glu Leu Gly Ala Leu Gly Ile
1               5                   10                  15

His Asp Val Gln Glu Val Val Tyr Asn Pro Ser Tyr Glu Leu Leu Phe
            20                  25                  30

Ala Glu Glu Thr Lys Pro Gly Leu Glu Gly Tyr Glu Lys Gly Thr Val
        35                  40                  45

Thr Asn Gln Gly Ala Val Ala Val Asn Thr Gly Ile Phe Thr Gly Arg
    50                  55                  60

Ser Pro Lys Asp Lys Tyr Ile Val Leu Asp Lys Thr Lys Asp Thr
65                  70                  75                  80

Val Trp Trp Thr Ser Glu Lys Val Lys Asn Asp Asn Lys Pro Met Ser
                85                  90                  95

Gln Asp Thr Trp Asn Ser Leu Lys Gly Leu Val Ala Asp Gln Leu Ser
            100                 105                 110

Gly Lys Arg Leu Phe Val Val Asp Ala Phe Cys Gly Ala Asn Lys Asp
        115                 120                 125

Thr Arg Leu Ala Val Arg Val Val Thr Glu Val Ala Trp Gln Ala His
    130                 135                 140

Phe Val Thr Asn Met Phe Ile Arg Pro Ser Ala Glu Glu Leu Lys Gly
145                 150                 155                 160

Phe Lys Pro Asp Phe Val Val Met Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Val Gln Leu Ile Gly Gly Thr Trp Tyr Gly Gly Glu
```

```
                195                 200                 205
Met Lys Lys Gly Met Phe Ser Met Met Asn Tyr Phe Leu Pro Leu Arg
    210                 215                 220

Gly Ile Ala Ser Met His Cys Ser Ala Asn Val Gly Lys Asp Gly Asp
225                 230                 235                 240

Thr Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Asp Glu Gly Val Phe Asn Phe Glu Gly Gly Cys Tyr Ala Lys Thr Ile
        275                 280                 285

Asn Leu Ser Ala Glu Asn Glu Pro Asp Ile Tyr Gly Ala Ile Lys Arg
    290                 295                 300

Asp Ala Leu Leu Glu Asn Val Val Val Leu Asp Asn Gly Asp Val Asp
305                 310                 315                 320

Tyr Ala Asp Gly Ser Lys Thr Glu Asn Thr Arg Val Ser Tyr Pro Ile
                325                 330                 335

Tyr His Ile Gln Asn Ile Val Lys Pro Val Ser Lys Ala Gly Pro Ala
            340                 345                 350

Thr Lys Val Ile Phe Leu Ser Ala Asp Ala Phe Gly Val Leu Pro Pro
        355                 360                 365

Val Ser Lys Leu Thr Pro Glu Gln Thr Lys Tyr Tyr Phe Leu Ser Gly
    370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Ala Ala Phe Leu Ser Leu His Pro
                405                 410                 415

Thr Gln Tyr Ala Glu Val Leu Val Lys Arg Met Gln Glu Ser Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Asp Lys Ala Glu Met Gly Ser Leu Pro Ile Phe Asp Phe Ser Ile
465                 470                 475                 480

Pro Lys Ala Leu Pro Gly Val Asn Pro Ala Ile Leu Asp Pro Arg Asp
                485                 490                 495

Thr Tyr Ala Asp Lys Ala Gln Trp Glu Glu Lys Ala Gln Asp Leu Ala
            500                 505                 510

Gly Arg Phe Val Lys Asn Phe Glu Lys Tyr Thr Gly Thr Ala Glu Gly
        515                 520                 525

Gln Ala Leu Val Ala Ala Gly Pro Lys Ala
    530                 535

<210> SEQ ID NO 6
<211> LENGTH: 1617
<212> TYPE: DNA
<213> ORGANISM: Mannheimia succiniciproduces

<400> SEQUENCE: 6
atgacagatc ttaatcaatt aactcaagaa cttggtgctt taggtattca tgatgtacaa    60
gaagttgtgt ataacccgag ctatgaactt cttttttgcgg aagaaaccaa accaggttta   120
gaaggttatg aaaaaggtac tgtgactaat caaggagcgg ttgctgtaaa taccggtatt   180
```

```
ttcaccggtc gttctccgaa agataaatat atcgttttag acgacaaaac taaagatacc    240
gtatggtgga ccagcgaaaa agttaaaaac gataacaaac caatgagcca agatacctgg    300
aacagtttga aaggtttagt tgccgatcaa cttttcggta acgtttatt tgttgttgac     360 gcattctgcg gcgcgaataa agatacgcgt ttagctgttc gtgtggttac tgaagttgca    420
tggcaggcgc attttgtaac aaatatgttt atccgcccct cagcggaaga attaaaaggt    480
ttcaaacctg atttcgtggt aatgaacggt gcaaaatgta caaatcctaa ctggaaagaa    540
caagggttaa attccgaaaa cttcgttgcg ttcaacatta cagaaggcgt tcaattaatc    600
ggcggtactt ggtacggtgg tgaaatgaaa aaaggtatgt tctcaatgat gaactacttc    660
ttaccgcttc gtggtattgc atcaatgcac tgttccgcaa acgttggtaa agacggcgat    720
accgcaattt tcttcggttt gtcaggcaca ggtaaaacga cattatcaac agatcctaaa    780
cgtcaactaa tcggtgatga cgaacacggt tgggacgatg aaggcgtatt taacttcgaa    840
ggtggttgct acgcgaaaac cattaactta tccgctgaaa acgagccgga tatctatggc    900
gctatcaaac gtgacgcatt attggaaaac gtggttgttt tagataacgg tgacgttgac    960
tatgcagacg gttccaaaac agaaaataca cgtgtttctt atccgattta tcacattcaa   1020
aatatcgtta aacctgtttc taaagctggt ccggcaacta agttatctt cttgtctgcc    1080 gatgcattcg gtgtattacc gccggtgtct aaattaactc cggaacaaac caaatactat   1140
ttcttatccg gtttcactgc gaaattagcg ggtacggaac gcggtattac agagcctaca   1200
ccaacattct ctgcatgttt tggtgcggct ttttaagct tgcatccgac acaatatgcc    1260
gaagtgttag taaaacgtat gcaagaatca ggtgcggaag cgtatcttgt taatacaggt   1320
tggaacggta ccggcaaacg tatctcaatt aaagataccc gtggtattat tgatgcaatt   1380
ttagacggct caattgataa agcggaaatg ggctcattac caatcttcga tttctcaatt   1440
cctaaagcat tacctggtgt taaccctgca atcttagatc gcgcgatac ttatgcggat    1500 aaagcgcaat gggaagaaaa agctcaagat cttgcaggtc gctttgtgaa aaactttgaa   1560
aaatataccg gtacggcgga aggtcaggca ttagttgctg ccggtcctaa agcataa      1617
```

<210> SEQ ID NO 7
<211> LENGTH: 1617
<212> TYPE: DNA
<213> ORGANISM: Artificial sequence
<220> FEATURE:
<223> OTHER INFORMATION: PEPCK A.s. optimised for A. niger

<400> SEQUENCE: 7

```
atgaccgacc tcaacaagct cgtcaaggaa ttgaacgacc ttggattgac tgatgtcaag     60
gagatcgtct acaaccccag ctacgagcag ctgttcgaag aagaaaccaa gcccggtctg    120
gaaggattcg acaagggcac cctcaccact ctgggtgctg ttgctgttga cactggtatc    180
ttcaccggcc gctctcccaa ggacaagtac attgtctgcg atgagactac caaggacacc    240
gtctggtgga actccgaggc tgccaagaac gacaacaagc ccatgactca ggaaacctgg    300
aagtccctcc gtgagcttgt tgccaagcag ctctccggca agcgtctgtt cgttgttgat    360
gctttctgcg gtgcctccga aagcaccgt atcggtgtcc gcatggtcac cgaggttgcc     420
tggcaggctc acttcgtcaa gaacatgttc atccgcccca ccgacgagga gctcaagaac    480
ttcaaggccg acttcaccgt cctcaacggt gccaagtgca ccaaccccaa ctggaaggag    540
cagggtctga actccgagaa cttcgtcgct ttcaacatca ccgagggtat ccagctgatc    600
ggtggtacct ggtacggtgg tgagatgaag aagggcatgt tctccatgat gaactacttc    660
```

```
cttcctctca agggtgttgc ctccatgcac tgctctgcca acgtcggcaa ggacggtgat    720
gttgccatct tcttcggtct gtctggcact ggcaagacca ccctctccac cgaccccaag    780
cgccagttga ttggtgatga cgaacacggc tgggatgaga gcggtgtttt caacttcgag    840
ggtggctgct acgccaagac catcaacctg agccaggaga cgagcctga catctacggt     900 gccatccgcc gtgatgctct cctcgagaac gttgttgtcc gcgccgatgg cagcgttgac    960
ttcgatgacg gcagcaagac cgagaacact cgtgtctcct accccatcta ccacattgac   1020
aacattgtcc gccctgtctc aaggccggt cacgccacca aggtcatctt cttgactgcc    1080
gatgctttcg gtgtccttcc tcctgtctcc aagctcaccc ccgagcagac cgaatactac   1140
ttcctgtctg gcttcactgc caagcttgct ggcaccgagc gtggtgtgac cgagcctact   1200
cctaccttct ctgcttgctt cggtgctgct ttcctctccc tgcacccat ccagtacgcc    1260 gatgtccttg ttgagcgcat gaaggcctcc ggtgctgagg cctacctggt caacactggc   1320
tggaacggca ctggcaagcg tatctccatc aaggacaccc gtggtatcat tgatgccatt   1380
ttggatggca gcattgagaa ggctgagatg ggtgagctcc ccatcttcaa cctggccatc   1440
cccaaggctc tccccggtgt tgaccccgcc atcctggacc ctcgtgacac ctacgccgac   1500
aaggcccagt ggcaggtcaa ggctgaggac cttgccaacc gcttcgtcaa gaacttcgtc   1560
aagtacactg ccaaccccga ggctgccaag ctcgtcggtg ctggtcccaa ggcgtaa      1617
```

<210> SEQ ID NO 8
<211> LENGTH: 1617
<212> TYPE: DNA
<213> ORGANISM: Artificial sequence
<220> FEATURE:
<223> OTHER INFORMATION: PEPCK M.s. optimised for A. niger

<400> SEQUENCE: 8

```
atgaccgacc tcaaccagct cacccaggag cttggtgctc ttggtatcca cgatgtgcag     60
gaggttgtct acaaccccag ctacgagctt ctgttcgctg aggaaaccaa gcccggtctg    120
gaaggatacg agaagggtac cgtcaccaac cagggtgctg ttgctgtcaa cactggtatc    180
ttcactggcc gctcccccaa ggacaagtac attgtcctcg atgacaagac caaggacacc    240
gtctggtgga cctccgagaa ggtcaagaac gacaacaagc ccatgagcca ggacacctgg    300
aactcgctga agggtcttgt tgccgaccag ctctccggca gcgtctgtt cgtcgtcgat     360 gctttctgcg gtgccaacaa ggacacccgc ctggccgtcc gcgttgtcac cgaggttgcc    420
tggcaggctc acttcgtcac caacatgttc atccgcccct gctgaggag ctcaagggt     480 ttcaagcccg acttcgtcgt catgaacggt gccaagtgca ccaaccccaa ctggaaggag    540
cagggtctga actccgagaa cttcgttgct ttcaacatca ccgagggtgt gcagctgatc    600
ggtggtacct ggtacggtgg tgagatgaag aagggcatgt tctccatgat gaactacttc    660
cttcctctcc gtggcattgc ctccatgcac tgctctgcca acgtcggcaa ggacggtgac    720
actgccatct tcttcggtct gtctggcact ggcaagacca ccctcagcac tgaccccaag    780
cgccagttga ttggtgatga cgaacacggc tgggatgatg agggtgtttt caacttcgag    840
ggtggctgct acgccaagac catcaacctg tctgctgaga cgagcctga catctacggt     900 gccatcaagc gtgatgccct cctcgagaac gttgttgtcc tcgacaacgg cgatgttgac    960
tacgccgatg cagcaagac tgagaacacc cgtgtcagct accccatcta ccacatccag   1020
aacattgtca agcctgtctc caaggccggt cctgccacca aggtcatctt cctgtctgcc   1080
```

| | |
|---|---|
| gatgctttcg gtgtccttcc tcctgtctcc aagctcaccc ccgagcagac caagtactac | 1140 |
| ttcctgtctg gcttcactgc caagctggct ggtactgagc gtggtatcac cgagcctact | 1200 |
| cccaccttct ccgcctgctt cggtgctgct ttcctgagct tgcaccccac ccagtacgct | 1260 |
| gaggttctcg tcaagcgcat gcaggagtcc ggtgctgagg cctacctcgt caacactggc | 1320 |
| tggaacggca ccggcaagcg tatctccatc aaggacaccc gtgtatcat tgatgccatt | 1380 |
| ttggatggct ccattgacaa ggctgagatg ggctccctcc ccatcttcga cttctccatc | 1440 |
| cccaaggccc tccccggtgt caaccccgcc atcctcgacc ctcgtgacac ctacgccgac | 1500 |
| aaggcccagt gggaggagaa ggcccaggat cttgctggcc gcttcgtcaa gaacttcgag | 1560 |
| aagtacactg gtactgcgga aggccaggcc ttggttgctg ctggtcctaa agcgtaa | 1617 |

<210> SEQ ID NO 9
<211> LENGTH: 1617
<212> TYPE: DNA
<213> ORGANISM: Artificial sequence
<220> FEATURE:
<223> OTHER INFORMATION: PEPCK A.s. optimised for S.cerevisiae

<400> SEQUENCE: 9

| | |
|---|---|
| atgactgatt tgaacaaatt ggtcaaggaa ttgaatgatt tgggtttgac tgacgtcaag | 60 |
| gaaattgtct acaacccatc ttacgaacaa ttattcgaag aagaaaccaa gccaggtttg | 120 |
| gaaggtttcg acaagggtac tttgaccact ttaggtgctg ttgctgttga caccggtatt | 180 |
| ttcaccggtc gttctccaaa ggacaaatac attgtttgtg atgaaaccac caaggacacc | 240 |
| gtctggtgga actctgaagc tgccaagaac gataacaagc caatgactca agaaacctgg | 300 |
| aaatctttga gagaattggt tgccaagcaa ttgtctggta agagattatt cgttgttgac | 360 |
| gctttctgtg gtgcttctga aaagcacaga attggtgtca gaatggtcac tgaagttgct | 420 |
| tggcaagctc atttcgtcaa gaacatgttc atcagaccaa ctgacgaaga attgaagaac | 480 |
| ttcaaggctg acttcaccgt tttgaatggt gccaagtgta ccaacccaaa ctggaaggaa | 540 |
| caaggtttga actctgaaaa ctttgttgct ttcaacatca ctgaaggtat ccaattgatt | 600 |
| ggtggtacct ggtacggtgg tgaaatgaag aagggtatgt tctccatgat gaactatttc | 660 |
| ttgccattga aggtgttgc ttccatgcac tgttctgcca atgtcggtaa ggatggtgac | 720 |
| gttgccatct tcttcggtct atccggtact ggtaagacca ctctatccac tgacccaaag | 780 |
| agacaattga ttggtgatga cgaacacggt tgggacgaat ctggtgtctt taactttgaa | 840 |
| ggtggttgtt acgccaagac catcaactta tctcaagaaa acgaaccaga tatctacggt | 900 |
| gccatccgtc gtgatgcttt gttggaaaac gttgttgtca gagctgacgg ttctgttgac | 960 |
| ttcgacgacg gttccaagac tgaaaacacc agagtttctt acccaatcta ccacattgac | 1020 |
| aacattgtca gacctgtttc caaggctggt cacgctacca aggttatctt cttgactgct | 1080 |
| gatgctttcg gtgtcttgcc acctgtttcc aaattgactc agaacaaac cgaatactac | 1140 |
| ttcttgtccg gtttcactgc caaattggct ggtactgaaa gaggtgtcac tgaaccaact | 1200 |
| ccaactttct ctgcttgttt cggtgctgct ttcttatctt tgcacccaat ccaatacgct | 1260 |
| gatgtcttgg ttgaaagaat gaaggcttct ggtgctgaag cttacttggt caacaccggt | 1320 |
| tggaacggta ccggtaagag aatctccatc aaggatacca gaggtatcat tgatgctatc | 1380 |
| ttggacggtt ccattgaaaa ggctgaaatg ggtgaattgc caatcttcaa cttggccatt | 1440 |
| ccaaaggctt tgccaggtgt tgacccagcc atccttagat caagagacac ctacgctgac | 1500 |
| aaggctcaat ggcaagtcaa ggctgaagat ttggctaaca gattcgtcaa gaactttgtc | 1560 |

```
aaatacactg ctaacccaga agctgccaaa ttggttggtg ctggtccaaa ggcttaa      1617
```

<210> SEQ ID NO 10
<211> LENGTH: 1617
<212> TYPE: DNA
<213> ORGANISM: Artificial sequence
<220> FEATURE:
<223> OTHER INFORMATION: PEPCK M.s. optimised for S. cerevisiae

<400> SEQUENCE: 10

```
atgaccgatt tgaaccaatt gactcaagaa ttgggtgctt tgggtattca cgatgtccaa        60
gaagttgtct acaacccatc ttacgaattg ttgtttgctg aagaaaccaa gccaggtttg       120
gaaggttacg aaaagggtac tgttaccaac caaggtgctg ttgctgtcaa caccggtatc       180
ttcaccggtc gttctccaaa ggacaaatac attgtcttgg atgacaagac caaggacact       240
gtctggtgga cttctgaaaa ggtcaagaac gacaacaaac caatgtccca agacacttgg       300
aactctttaa agggtttagt cgctgaccaa ttgtctggta agagattatt cgttgtcgat       360
gctttctgtg gtgccaacaa ggacaccaga ttagctgtca gagttgtcac tgaagttgct       420
tggcaagctc acttcgttac caacatgttc atcagaccat ctgctgaaga attgaaaggt       480
ttcaagccag atttcgttgt catgaacggt gccaaatgta ccaacccaaa ctggaaggaa       540
caaggtttga actctgaaaa ctttgttgct ttcaacatca ctgaaggtgt tcaattgatt       600
ggtggtacct ggtacggtgg tgaaatgaag aagggtatgt ctccatgat gaactacttc        660
ttgccattga aggtattgc ttccatgcac tgttctgcca atgtcggtaa ggacggtgac        720
actgccatct tcttcggtct atccggtacc ggtaagacca ctttgtccac tgacccaaag       780
agacaattga ttggtgatga cgaacacggt tgggatgacg aaggtgtttt caactttgaa       840
ggtggttgtt acgccaagac catcaactta tctgctgaaa atgaaccaga tatctacggt       900
gccatcaagc gtgacgctct attggaaaac gttgttgttt tggacaatgg tgacgtcgat       960
tatgctgacg gttccaagac tgaaaacacc agagtttctt acccaatcta ccatattcaa      1020
aacattgtca gccagtttc caaggctggt ccagctacca agttatctt cttgtctgct       1080
gatgctttcg gtgttttgcc tcctgtttcc aagttgactc agaacaaac caagtactac       1140
ttcttgtctg gtttcaccgc caagttggct ggtactgaaa aggtatcac tgaaccaact       1200
ccaactttct ctgcttgttt cggtgctgcc tttttgtctt gcacccaac tcaatacgct       1260
gaagttttgg tcaagagaat gcaagaatct ggtgctgaag cttacttggt caacactggt       1320
tggaacggta ccggtaagag aatctccatc aaagatacca gaggtatcat cgatgccatc       1380
ttggatggtt ccattgacaa ggctgaaatg ggttctttgc aatttttcga tttctccatt       1440
ccaaaggctt tgccaggtgt caacccagcc atcttagacc aagagacac ctacgctgac       1500
aaagctcaat gggaagaaaa aggtcaagac ttggctggta gattcgtcaa gaacttcgaa       1560
aaatacactg gtactgctga aggtcaagct tggttgctg ctggtccaaa ggcctaa         1617
```

<210> SEQ ID NO 11
<211> LENGTH: 898
<212> TYPE: DNA
<213> ORGANISM: Artificial sequence
<220> FEATURE:
<223> OTHER INFORMATION: GPDA promotor

<400> SEQUENCE: 11

```
tcagcgtcca attcgagctc tgtacagtga ccggtgactc tttctggcat gcggagacac        60
```

```
ggacggtcgc agagaggagg gctgagtaat aagcgcactc atgtcagctc tggcgctctg      120
aggtgcagtg gatgattatt aatccgggac cggccgcccc tccgcccga agtggaaagg       180 ctggtgtgcc cctcgttgac caagaatcta ttgcatcatc ggagaatatg gagcttcatc     240
gaatcaccgg cagtaagcga aggagaatgt gaagccaggg gtgtatagcc gtcggcgaaa     300
tagcatgcca ttaacctagg tacagaagtc caattgcttc cgatctggta aaagattcac     360
gagatagtac cttctccgaa gtaggtagag cgagtacccg gcgcgtaagc tccctaattg     420
gcccatccgg catctgtagg gcgtccaaat atcgtgcctc tcctgctttg cccggtgtat     480
gaaaccggaa aggccgctca ggagctggcc agcggcgcag accgggaaca aagctggca     540 gtcgacccat ccggtgctct gcactcgacc tgctgaggtc cctcagtccc tggtaggcag     600
cttttgcccg tctgtccgcc cggtgtgtcg gcggggttga caaggtcgtt gcgtcagtcc     660
aacatttgtt gccatatttt cctgctctcc ccaccagctg ctctttttct ttctctttct     720
tttcccatct tcagtatatt catcttccca tccaagaacc tttatttccc ctaagtaagt     780
actttgctac atccatactc catccttccc atcccttatt cctttgaacc tttcagttcg     840
agctttccca cttcatcgca gcttgactaa cagctacccc gcttgagcca ccgtcaaa      898

<210> SEQ ID NO 12
<211> LENGTH: 1000
<212> TYPE: DNA
<213> ORGANISM: Artificial sequence
<220> FEATURE:
<223> OTHER INFORMATION: TDH1 promotor

<400> SEQUENCE: 12
cttccctttt acagtgcttc ggaaaagcac agcgttgtcc aagggaacaa ttttcttca      60 agttaatgca taagaaatat cttttttat gtttagctaa gtaaaagcag cttggagtaa     120
aaaaaaaaat gagtaaattt ctcgatggat tagtttctca caggtaacat aacaaaaacc     180
aagaaaagcc cgcttctgaa aactacagtt gacttgtatg ctaaagggcc agactaatgg    240
gaggagaaaa agaaacgaat gtatatgctc atttacactc tatatcacca tatggaggat    300
aagttgggct gagcttctga tccaatttat tctatccatt agttgctgat atgtcccacc    360
agccaacact tgatagtatc tactcgccat tcacttccag cagcgccagt agggttgttg    420
agcttagtaa aaatgtgcgc accacaagcc tacatgactc cacgtcacat gaaaccacac    480
cgtggggcct tgttgcgcta ggaataggat atgcgacgaa gacgcttctg cttagtaacc    540
acaccacatt ttcaggggt cgatctgctt gcttccttta ctgtcacgag cggcccataa     600
tcgcgctttt tttttaaaag gcgcgagaca gcaaacagga agctcgggtt tcaaccttcg    660
gagtggtcgc agatctggag actggatctt tacaatacag taaggcaagc caccatctgc   720
ttcttaggtg catgcgacgg tatccacgtg cagaacaaca tagtctgaag aaggggggga    780
ggagcatgtt cattctctgt agcagtaaga gcttggtgat aatgaccaaa actggagtct   840
cgaaatcata taaatagaca atatatttc acacaatgag atttgtagta cagttctatt    900
ctctctcttg cataaataag aaattcatca agaacttggt ttgatatttc accaacacac    960
acaaaaaaca gtacttcact aaatttacac acaaaacaaa                         1000

<210> SEQ ID NO 13
<211> LENGTH: 500
<212> TYPE: DNA
<213> ORGANISM: Artificial sequence
<220> FEATURE:
<223> OTHER INFORMATION: TDH1 terminator
```

<400> SEQUENCE: 13

```
ataaagcaat cttgatgagg ataatgattt tttttttgaat atacataaat actaccgttt      60
ttctgctaga ttttgtgaag acgtaaataa gtacatatta cttttttaagc caagacaaga    120 ttaagcatta actttaccct tttctcttct aagtttcaat actagttatc actgtttaaa    180
agttatggcg agaacgtcgg cggttaaaat atattaccct gaacgtggtg aattgaagtt    240
ctaggatggt ttaaagattt ttccttttttg ggaaataagt aaacaatata ttgctgcctt    300
tgcaaaacgc atacccacaa atatgtgac tattggcaaa gaacgcatta tcctttgaag    360
aggtggatac tgatactaag agagtctcta ttccggctcc acttttagtc cagagattac    420
ttgtcttctt acgtatcaga acaagaaagc atttccaaag taattgcatt tgcccttgag    480
cagtatatat atactaagaa                                                 500
```

<210> SEQ ID NO 14
<211> LENGTH: 340
<212> TYPE: PRT
<213> ORGANISM: Artificial sequence
<220> FEATURE:
<223> OTHER INFORMATION: MDH3 S. cerevisiae lacking SKL targeting signal

<400> SEQUENCE: 14

```
Met Val Lys Val Ala Ile Leu Gly Ala Ser Gly Gly Val Gly Gln Pro
  1               5                  10                  15

Leu Ser Leu Leu Leu Lys Leu Ser Pro Tyr Val Ser Glu Leu Ala Leu
             20                  25                  30

Tyr Asp Ile Arg Ala Ala Glu Gly Ile Gly Lys Asp Leu Ser His Ile
         35                  40                  45

Asn Thr Asn Ser Ser Cys Val Gly Tyr Asp Lys Asp Ser Ile Glu Asn
     50                  55                  60

Thr Leu Ser Asn Ala Gln Val Val Leu Ile Pro Ala Gly Val Pro Arg
 65                  70                  75                  80

Lys Pro Gly Leu Thr Arg Asp Asp Leu Phe Lys Met Asn Ala Gly Ile
                 85                  90                  95

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
        115                 120                 125

Glu Thr Leu Lys Lys Met Gly Lys Phe Lys Pro Gly Asn Val Met Gly
    130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
                165                 170                 175

Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
        195                 200                 205

Tyr Glu His Phe Ile His Arg Val Gln Phe Gly Gly Asp Glu Ile Val
    210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255
```

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
        275                 280                 285

Phe Ser Leu Pro Ile Val Leu Arg Asn Gly Ser Val Val Ser Ile Asp
        290                 295                 300

Thr Ser Val Leu Glu Lys Leu Ser Pro Arg Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser
            340

<210> SEQ ID NO 15
<211> LENGTH: 1023
<212> TYPE: DNA
<213> ORGANISM: Artificial sequence
<220> FEATURE:
<223> OTHER INFORMATION: MDH3 nt S. cerevisiae lacking nt encoding SKL
      targeting signal

<400> SEQUENCE: 15
atggttaagg ttgccatctt aggtgcttct ggtggtgtcg gtcaaccatt atctctatta      60
ttgaaattgt ctccatacgt ttctgaattg gctttgtacg atatcagagc tgctgaaggt     120
attggtaagg atttgtccca catcaacacc aactcctctt gtgttggtta cgacaaggat     180
tccatcgaaa acactttgtc caatgctcaa gttgtcttga ttccagctgg tgttccaaga     240
aagccaggtt tgaccagaga tgatttgttc aagatgaacg ctggtatcgt taagtctttg     300
gttactgctg tcggtaaatt tgccccaaac gctcgtatct tagtcatctc caaccctgtt     360
aactctttgg ttccaattgc cgttgaaact ttgaagaaga tgggtaagtt caagccaggt     420
aacgttatgg gtgtcaccaa cttggatttg gtcagagctg aaactttctt ggttgactac     480
ttgatgttga gaacccaaa gatcggtcaa gaacaagaca gaccaccat gcacagaaag      540 gtcaccgtca tcggtggtca ctctggtgaa accatcattc caatcatcac tgacaaatcc     600
ttggttttcc aattggacaa gcaatacgaa catttcatcc acagagtcca attcggtggt     660
gacgaaattg tcaaggccaa gcaaggtgcc ggttctgcta ccttgtccat ggctttcgct     720
ggtgccaaat tgctgaaga gtcttacgt tctttccaca cgaaaagcc agaaactgaa       780 tctttgtctg ctttcgtcta cttgccaggt ttgaagaacg gtaagaaggc tcaacaatta    840
gtcggtgaca actccattga atacttctct ttgccaattg ttttgagaaa cggttccgtt     900
gtttccattg acacttctgt tttggaaaaa ttgtctccaa gagaagaaca attggtcaac     960
actgctgtca ggaattgag aaagaacatt gaaaagggta gtctttcat cttggacagt    1020 taa                                                                  1023

<210> SEQ ID NO 16
<211> LENGTH: 472
<212> TYPE: PRT
<213> ORGANISM: Artificial sequence
<220> FEATURE:
<223> OTHER INFORMATION: Fumarase R. oryzae lacking first 23 aa + M

<400> SEQUENCE: 16

Met Ser Ser Ala Ser Ala Ala Leu Gln Lys Phe Arg Ala Glu Arg Asp
1               5                   10                  15

Thr Phe Gly Asp Leu Gln Val Pro Ala Asp Arg Tyr Trp Gly Ala Gln

```
                20                  25                  30
Thr Gln Arg Ser Leu Gln Asn Phe Asp Ile Gly Gly Pro Thr Glu Arg
            35                  40                  45
Met Pro Glu Pro Leu Ile Arg Ala Phe Gly Val Leu Lys Lys Ala Ala
 50                  55                  60
Ala Thr Val Asn Met Thr Tyr Gly Leu Asp Pro Lys Val Gly Glu Ala
 65                  70                  75                  80
Ile Gln Lys Ala Ala Asp Glu Val Ile Asp Gly Ser Leu Ile Asp His
                85                  90                  95
Phe Pro Leu Val Val Trp Gln Thr Gly Ser Gly Thr Gln Thr Lys Met
            100                 105                 110
Asn Val Asn Glu Val Ile Ser Asn Arg Ala Ile Glu Leu Leu Gly Gly
        115                 120                 125
Glu Leu Gly Ser Lys Ala Pro Val His Pro Asn Asp His Val Asn Met
    130                 135                 140
Ser Gln Ser Ser Asn Asp Thr Phe Pro Thr Ala Met His Val Ala Ala
145                 150                 155                 160
Val Val Glu Ile His Gly Arg Leu Ile Pro Ala Leu Thr Thr Leu Arg
                165                 170                 175
Asp Ala Leu Gln Ala Lys Ser Ala Glu Phe Glu His Ile Ile Lys Ile
            180                 185                 190
Gly Arg Thr His Leu Gln Asp Ala Thr Pro Leu Thr Leu Gly Gln Glu
        195                 200                 205
Phe Ser Gly Tyr Thr Gln Gln Leu Thr Tyr Gly Ile Ala Arg Val Gln
    210                 215                 220
Gly Thr Leu Glu Arg Leu Tyr Asn Leu Ala Gln Gly Gly Thr Ala Val
225                 230                 235                 240
Gly Thr Gly Leu Asn Thr Arg Lys Gly Phe Asp Ala Lys Val Ala Glu
                245                 250                 255
Ala Ile Ala Ser Ile Thr Gly Leu Pro Phe Lys Thr Ala Pro Asn Lys
            260                 265                 270
Phe Glu Ala Leu Ala Ala His Asp Ala Leu Val Glu Ala His Gly Ala
        275                 280                 285
Leu Asn Thr Val Ala Cys Ser Leu Met Lys Ile Ala Asn Asp Ile Arg
    290                 295                 300
Tyr Leu Gly Ser Gly Pro Arg Cys Gly Leu Gly Glu Leu Ser Leu Pro
305                 310                 315                 320
Glu Asn Glu Pro Gly Ser Ser Ile Met Pro Gly Lys Val Asn Pro Thr
                325                 330                 335
Gln Cys Glu Ala Met Thr Met Val Cys Ala Gln Val Met Gly Asn Asn
            340                 345                 350
Thr Ala Ile Ser Val Ala Gly Ser Asn Gly Gln Phe Glu Leu Asn Val
        355                 360                 365
Phe Lys Pro Val Met Ile Lys Asn Leu Ile Gln Ser Ile Arg Leu Ile
    370                 375                 380
Ser Asp Ala Ser Ile Ser Phe Thr Lys Asn Cys Val Val Gly Ile Glu
385                 390                 395                 400
Ala Asn Glu Lys Lys Ile Ser Ser Ile Met Asn Glu Ser Leu Met Leu
                405                 410                 415
Val Thr Ala Leu Asn Pro His Ile Gly Tyr Asp Lys Ala Ala Lys Cys
            420                 425                 430
Ala Lys Lys Ala His Lys Glu Gly Thr Thr Leu Lys Glu Ala Ala Leu
        435                 440                 445
```

Ser Leu Gly Tyr Leu Thr Ser Glu Glu Phe Asp Gln Trp Val Arg Pro
    450                 455                 460

Glu Asp Met Ile Ser Ala Lys Asp
465                 470

<210> SEQ ID NO 17
<211> LENGTH: 1419
<212> TYPE: DNA
<213> ORGANISM: Artificial sequence
<220> FEATURE:
<223> OTHER INFORMATION: FumR nt cpo for S. cerevisiae lacking nt
      encoding first 23 aa + M

<400> SEQUENCE: 17

| | | | | | | |
|---|---|---|---|---|---|---|
| atgtcctctg | cttctgctgc | tttgcaaaaa | ttcagagctg | aaagagatac | cttcggtgac | 60 |
| ttgcaagttc | cagctgaccg | ttactggggt | gctcaaactc | aaagatcttt | gcaaaacttt | 120 |
| gacattggtg | gtccaactga | aagaatgcca | gaaccattaa | tcagagcttt | cggtgttttg | 180 |
| aagaaggctg | ctgccaccgt | caacatgacc | tacggtttgg | acccaaaggt | tggtgaagcc | 240 |
| atccaaaagg | ctgctgacga | agttatcgat | ggttctttga | ttgaccattt | cccattggtt | 300 |
| gtctggcaaa | ccggttctgg | tactcaaacc | aagatgaacg | tcaatgaagt | catctccaac | 360 |
| agagccattg | aattgttggg | tggtgaatta | ggttccaagg | ctccagtcca | cccaaacgat | 420 |
| catgtcaaca | tgtctcaatc | ttccaacgac | actttcccaa | ctgccatgca | cgttgctgcc | 480 |
| gttgttgaaa | ttcacggtag | attgattcca | gctttgacca | ctttgagaga | tgctttgcaa | 540 |
| gccaaatctg | ctgaattcga | acacatcatc | aagattggta | gaacccactt | gcaagatgct | 600 |
| accccattga | ctttaggtca | agaattctcc | ggttacactc | aacaattgac | ctacggtatt | 660 |
| gctcgtgttc | aaggtacttt | ggaaagatta | tacaacttgg | ctcaaggtgg | tactgctgtc | 720 |
| ggtactggtt | tgaacaccag | aaagggtttc | gatgccaagg | ttgctgaagc | cattgcttcc | 780 |
| atcactggtt | taccattcaa | gaccgctcca | aacaaattcg | aagctttggc | tgctcacgac | 840 |
| gctttggttg | aagctcacgg | tgcttttgaac | accgttgctt | gttctttgat | gaagattgcc | 900 |
| aacgatatcc | gttacttggg | ttctggtcca | agatgtggtt | taggtgaatt | gtctctacca | 960 |
| gaaaacgaac | aggttcttc | catcatgcca | ggtaaggtca | acccaactca | atgtgaagct | 1020 |
| atgaccatgg | tttgtgctca | agtcatgggt | aacaacactg | ccatctctgt | tgctggttcc | 1080 |
| aacggtcaat | tcgaattgaa | tgtctttaaa | ccagtcatga | tcaagaactt | gatccaatcc | 1140 |
| atcagattaa | tctctgacgc | ttccatctct | ttcaccaaga | actgtgttgt | cggtattgaa | 1200 |
| gctaacgaaa | agaagatctc | ctccatcatg | aacgaatctt | tgatgttggt | cactgctttg | 1260 |
| aaccctcaca | ttggttacga | caaggctgcc | aagtgtgcca | agaaggctca | caaggaaggt | 1320 |
| accactttga | agaagctgc | tctatctttg | ggttacttga | cctctgaaga | attcgaccaa | 1380 |
| tgggttagac | tgaggacat | gatttctgcc | aaggattaa | | | 1419 |

<210> SEQ ID NO 18
<211> LENGTH: 600
<212> TYPE: DNA
<213> ORGANISM: Artificial sequence
<220> FEATURE:
<223> OTHER INFORMATION: TDH3 promotor

<400> SEQUENCE: 18

| | | | | | | |
|---|---|---|---|---|---|---|
| ttagtcaaaa | aattagcctt | ttaattctgc | tgtaacccgt | acatgcccaa | aatagggggc | 60 |
| gggttacaca | gaatatataa | catcgtaggt | gtctgggtga | acagtttatt | cctggcatcc | 120 |

```
actaaatata atggagcccg cttttaagc tggcatccag aaaaaaaaag aatcccagca      180
ccaaaatatt gttttcttca ccaaccatca gttcataggt ccattctctt agcgcaacta      240
cagagaacag gggcacaaac aggcaaaaaa cgggcacaac ctcaatggag tgatgcaacc     300
tgcctggagt aaatgatgac acaaggcaat tgacccacgc atgtatctat ctcatttct      360 tacaccttct attaccttct gctctctctg atttggaaaa agctgaaaaa aaaggttgaa     420
accagttccc tgaaattatt cccctacttg actaataagt atataaagac ggtaggtatt     480
gattgtaatt ctgtaaatct atttcttaaa cttcttaaat tctactttta tagttagtct      540
tttttttagt tttaaaacac caagaactta gtttcgaata acacacata aacaaacaaa       600

<210> SEQ ID NO 19
<211> LENGTH: 300
<212> TYPE: DNA
<213> ORGANISM: Artificial sequence
<220> FEATURE:
<223> OTHER INFORMATION: TDH3 terminator

<400> SEQUENCE: 19
gtgaatttac tttaaatctt gcatttaaat aaattttctt tttatagctt tatgacttag      60
tttcaattta tatactattt taatgacatt ttcgattcat tgattgaaag ctttgtgttt     120
tttcttgatg cgctattgca ttgttcttgt ctttttcgcc acatgtaata tctgtagtag    180
atacctgata cattgtggat gctgagtgaa attttagtta ataatggagg cgctcttaat     240
aattttgggg atattggctt ttttttttaa agtttacaaa tgaattttt ccgccaggat     300

<210> SEQ ID NO 20
<211> LENGTH: 1966
<212> TYPE: DNA
<213> ORGANISM: Artificial sequence
<220> FEATURE:
<223> OTHER INFORMATION: TDH3p-MDH3-TDH3t synthetic construct

<400> SEQUENCE: 20
ggatccggcg cgccacgcgt ggccggcctt agtcaaaaaa ttagcctttt aattctgctg      60
taacccgtac atgcccaaaa taggggggcgg gttacacaga atatataaca tcgtaggtgt    120
ctgggtgaac agtttattcc tggcatccac taaatataat ggagcccgct ttttaagctg    180
gcatccagaa aaaaaagaa tcccagcacc aaaatattgt tttcttcacc aaccatcagt     240
tcataggtcc attctcttag cgcaactaca gagaacaggg gcacaaacag gcaaaaaacg    300
ggcacaacct caatggagtg atgcaacctg cctggagtaa atgatgacac aaggcaattg    360
acccacgcat gtatctatct catttcttca ccttctat taccttctgc tctctctgat      420
ttggaaaaag ctgaaaaaaa aggttgaaac cagttccctg aaattattcc ctacttgac     480 taataagtat ataagacgg taggtattga ttgtaattct gtaaatctat ttcttaaact     540
tcttaaattc tactttata gttagtcttt ttttagttt taaaacacca agaacttagt     600
ttcgaataaa cacacataaa caaacaaaat ggttaaggtt gccatcttag gtgcttctgg    660
tggtgtcggt caaccattat ctctattatt gaaattgtct ccatacgttt ctgaattggc     720
tttgtacgat atcagagctg ctgaaggtat tggtaaggat ttgtcccaca tcaacaccaa    780
ctcctcttgt gttggttacg acaaggattc catcgaaaac actttgtcca atgctcaagt    840
tgtcttgatt ccagctggtg ttccaagaaa gccaggttg accagagatg atttgttcaa    900
gatgaacgct ggtatcgtta agtctttggt tactgctgtc ggtaaatttg ccccaaacgc    960
```

```
tcgtatctta gtcatctcca accctgttaa ctctttggtt ccaattgccg ttgaaacttt     1020
gaagaagatg ggtaagttca agccaggtaa cgttatgggt gtcaccaact tggatttggt     1080
cagagctgaa actttcttgg ttgactactt gatgttgaag aacccaaaga tcggtcaaga     1140
acaagacaag accaccatgc acagaaaggt caccgtcatc ggtggtcact ctggtgaaac     1200
catcattcca atcatcactg acaaatcctt ggttttccaa ttggacaagc aatacgaaca     1260
tttcatccac agagtccaat cggtggtga cgaaattgtc aaggccaagc aaggtgccgg      1320
ttctgctacc ttgtccatgg cttttcgctgg tgccaaattt gctgaagaag tcttacgttc    1380
tttccacaac gaaaagccag aaactgaatc tttgtctgct ttcgtctact tgccaggttt     1440
gaagaacggt aagaaggctc aacaattagt cggtgacaac tccattgaat acttctcttt     1500
gccaattgtt ttgagaaacg gttccgttgt ttccattgac acttctgttt tggaaaaatt     1560
gtctccaaga gaagaacaat tggtcaacac tgctgtcaag gaattgagaa agaacattga     1620
aaagggtaag tctttcatct tggacagtta aggtgaattt actttaaatc ttgcatttaa     1680
ataaattttc ttttatagc tttatgactt agtttcaatt tatatactat tttaatgaca     1740
ttttcgattc attgattgaa agctttgtgt tttttcttga tgcgctattg cattgttctt     1800 gtcttttcg ccacatgtaa tatctgtagt agatacctga tacattgtgg atgctgagtg      1860 aaatttagt taataatgga ggcgctctta ataattttgg ggatattggc ttttttttt       1920 aaagtttaca aatgaatttt ttccgccagg atgggcccgc ggccgc                    1966

<210> SEQ ID NO 21
<211> LENGTH: 2950
<212> TYPE: DNA
<213> ORGANISM: Artificial sequence
<220> FEATURE:
<223> OTHER INFORMATION: TDH1p-FUMR-TDH1t synthetic construct

<400> SEQUENCE: 21
ggatcccttc cctttacag tgcttcggaa aagcacagcg ttgtccaagg gaacaatttt       60
tcttcaagtt aatgcataag aaatatcttt tttatgtttt agctaagtaa aagcagcttg     120
gagtaaaaaa aaaaatgagt aaatttctcg atggattagt ttctcacagg taacataaca    180
aaaaccaaga aaagcccgct tctgaaaact acagttgact tgtatgctaa agggccagac    240
taatgggagg agaaaaagaa acgaatgtat atgctcattt acactctata tcaccatatg    300
gaggataagt tgggctgagc ttctgatcca atttattcta tccattagtt gctgatatgt    360
cccaccagcc aacacttgat agtatctact cgccattcac ttccagcagc gccagtaggg    420
ttgttgagct tagtaaaaat gtgcgcacca caagcctaca tgactccacg tcacatgaaa    480
ccacaccgtg gggccttgtt gcgctaggaa taggatatgc gacgaagacg cttctgctta    540
gtaaccacac cacattttca ggggtcgat ctgcttgctt cctttactgt cacgagcggc      600
ccataatcgc gcttttttt taaaaggcgc gagacagcaa acaggaagct cgggtttcaa      660
ccttcggagt ggtcgcagat ctggagactg atctttaca atacagtaag gcaagccacc     720
atctgcttct taggtgcatg cgacggtatc cacgtgcaga acaacatagt ctgaagaagg    780
gggggaggag catgttcatt ctctgtagca gtaagagctt ggtgataatg accaaaactg    840
gagtctcgaa atcatataaa tagacaatat attttcacac aatgagattt gtagtacagt    900
tctattctct ctcttgcata aataagaaat tcatcaagaa cttggtttga tatttcacca    960
acacacacaa aaaacagtac ttcactaaat ttacacacaa aacaaaatgt cctctgcttc    1020
tgctgctttg caaaaattca gagctgaaag agatccttc ggtgacttgc aagttccagc     1080
```

```
tgaccgttac tggggtgctc aaactcaaag atctttgcaa aactttgaca ttggtggtcc    1140
aactgaaaga atgccagaac cattaatcag agctttcggt gttttgaaga aggctgctgc    1200
caccgtcaac atgacctacg gtttggaccc aaaggttggt gaagccatcc aaaaggctgc    1260
tgacgaagtt atcgatggtt ctttgattga ccatttccca ttggttgtct ggcaaaccgg    1320
ttctggtact caaaccaaga tgaacgtcaa tgaagtcatc tccaacagag ccattgaatt    1380
gttgggtggt gaattaggtt ccaaggctcc agtccaccca acgatcatg tcaacatgtc     1440 tcaatcttcc aacgacactt tcccaactgc catgcacgtt gctgccgttg ttgaaattca    1500
cggtagattg attccagctt tgaccacttt gagagatgct ttgcaagcca aatctgctga    1560
attcgaacac atcatcaaga ttggtagaac ccacttgcaa gatgctaccc cattgacttt    1620
aggtcaagaa ttctccggtt acactcaaca attgacctac ggtattgctc gtgttcaagg    1680
tactttggaa agattataca acttggctca aggtggtact gctgtcggta ctggtttgaa    1740
caccagaaag ggtttcgatg ccaaggttgc tgaagccatt gcttccatca ctggtttacc    1800
attcaagacc gctccaaaca aattcgaagc tttggctgct cacgacgctt tggttgaagc    1860
tcacggtgct ttgaacaccg ttgcttgttc tttgatgaag attgccaacg atatccgtta    1920
cttgggttct ggtccaagat gtggtttagg tgaattgtct ctaccagaaa acgaaccagg    1980
ttcttccatc atgccaggta aggtcaaccc aactcaatgt gaagctatga ccatggtttg    2040
tgctcaagtc atgggtaaca acactgccat ctctgttgct ggttccaacg gtcaattcga    2100
attgaatgtc tttaaaccag tcatgatcaa gaacttgatc caatccatca gattaatctc    2160
tgacgcttcc atctctttca ccaagaactg tgttgtcggt attgaagcta acgaaaagaa    2220
gatctcctcc atcatgaacg aatctttgat gttggtcact gctttgaacc ctcacattgg    2280
ttacgacaag gctgccaagt gtgccaagaa ggctcacaag gaaggtacca ctttgaaaga    2340
agctgctcta tctttgggtt acttgacctc tgaagaattc gaccaatggg ttagacctga    2400
ggacatgatt tctgccaagg attaaggccc gggcataaag caatcttgat gaggataatg    2460 atttttttt gaatatacat aaatactacc gttttctgc tagattttgt gaagacgtaa     2520
ataagtacat attactttt aagccaagac aagattaagc attaactta ccctttctc      2580 ttctaagttt caatactagt tatcactgtt taaaagttat ggcgagaacg tcggcggtta    2640
aaatatatta ccctgaacgt ggtgaattga agttctagga tggtttaaag attttttcctt   2700 tttgggaaat aagtaaacaa tatattgctg cctttgcaaa acgcacatac ccacaatatg    2760
tgactattgg caaagaacgc attatccttt gaagaggtgg atactgatac taagagagtc    2820
tctattccgg ctccactttt agtccagaga ttacttgtct tcttacgtat cagaacaaga    2880
aagcatttcc aaagtaattg catttgccct tgagcagtat atatatacta agaaggcgcg    2940
ccgcggccgc                                                           2950
```

<210> SEQ ID NO 22
<211> LENGTH: 1139
<212> TYPE: PRT
<213> ORGANISM: Artificial sequence
<220> FEATURE:
<223> OTHER INFORMATION: FRDg Trypanosoma brucei lacking C-terminal
    targeting sequence SKI

<400> SEQUENCE: 22

Met Val Asp Gly Arg Ser Ser Ala Ser Ile Val Ala Val Asp Pro Glu
1               5                   10                  15

```
Arg Ala Ala Arg Glu Arg Asp Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

Cys Phe Asp Pro Ser Thr Ala Pro Val Ala Lys Ala Leu Arg Glu Ile
    130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
        195                 200                 205

Phe Gln Asn Val Phe Phe Asp Trp Gly Gly Asp Cys Arg Ala Ser Gly
    210                 215                 220

Met Asn Ala Arg Asn Thr Pro Trp Val Val Gly Ile Thr Arg Pro Pro
225                 230                 235                 240

Ser Leu Asp Met Leu Pro Asn Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
        275                 280                 285

Trp Lys Gly Lys Glu Leu Met Lys Pro Ser Gln Ser Asn Ile Ala Gln
    290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Arg Val Tyr Val
            340                 345                 350

Arg Glu Asn Glu Arg Val Ala Lys Met Phe Glu Ile Ala Thr Glu Asp
        355                 360                 365

Ala Glu Met Arg Lys Arg Ile Ser Asn Thr Leu Pro Ala Arg Val
    370                 375                 380

Ile Val Val Gly Gly Gly Leu Ala Gly Leu Ser Ala Ala Ile Glu Ala
385                 390                 395                 400

Ala Gly Cys Gly Ala Gln Val Val Leu Met Glu Lys Glu Ala Lys Leu
                405                 410                 415

Gly Gly Asn Ser Ala Lys Ala Thr Ser Gly Ile Asn Gly Trp Gly Thr
            420                 425                 430

Arg Ala Gln Ala Lys Ala Ser Ile Val Asp Gly Gly Lys Tyr Phe Glu
```

-continued

```
            435                 440                 445
Arg Asp Thr Tyr Lys Ser Gly Ile Gly Gly Asn Thr Asp Pro Ala Leu
450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                    485                 490                 495

Arg Lys Arg Thr His Arg Ala Pro Asp Lys Lys Asp Gly Thr Pro Leu
                500                 505                 510

Pro Ile Gly Phe Thr Ile Met Lys Thr Leu Glu Asp His Val Arg Gly
            515                 520                 525

Asn Leu Ser Gly Arg Ile Thr Ile Met Glu Asn Cys Ser Val Thr Ser
530                 535                 540

Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Gly Lys Thr Thr Ile
                565                 570                 575

Leu Ala Asp Ala Val Ile Leu Ala Thr Gly Gly Phe Ser Asn Asp Lys
                580                 585                 590

Thr Ala Asp Ser Leu Leu Arg Glu His Ala Pro His Leu Val Asn Phe
            595                 600                 605

Pro Thr Thr Asn Gly Pro Trp Ala Thr Gly Asp Gly Val Lys Leu Ala
610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                645                 650                 655

Leu Gly Pro Glu Ala Leu Arg Gly Ser Gly Gly Val Leu Leu Asn Lys
                660                 665                 670

Gln Gly Lys Arg Phe Val Asn Glu Leu Asp Leu Arg Ser Val Val Ser
            675                 680                 685

Lys Ala Ile Met Glu Gln Gly Ala Glu Tyr Pro Gly Ser Gly Gly Ser
690                 695                 700

Met Phe Ala Tyr Cys Val Leu Asn Ala Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
                740                 745                 750

Ser Val Gln Gln Thr Leu Glu Glu Tyr Glu Arg Leu Ser Ile Ser Gln
            755                 760                 765

Arg Ser Cys Pro Ile Thr Arg Lys Ser Val Tyr Pro Cys Val Leu Gly
770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

Asn Thr Ser Ser Arg Ala Pro Leu Ser His Ser Asn Pro Ile Leu Gly
                820                 825                 830

Leu Phe Gly Ala Gly Glu Val Thr Gly Gly Val His Gly Gly Asn Arg
            835                 840                 845

Leu Gly Gly Asn Ser Leu Leu Glu Cys Val Val Phe Gly Arg Ile Ala
850                 855                 860
```

Gly Asp Arg Ala Ser Thr Ile Leu Gln Arg Lys Ser Ser Ala Leu Ser
865                 870                 875                 880

Phe Lys Val Trp Thr Thr Val Val Leu Arg Glu Val Arg Glu Gly Gly
            885                 890                 895

Val Tyr Gly Ala Gly Ser Arg Val Leu Arg Phe Asn Leu Pro Gly Ala
        900                 905                 910

Leu Gln Arg Ser Gly Leu Ser Leu Gly Gln Phe Ile Ala Ile Arg Gly
            915                 920                 925

Asp Trp Asp Gly Gln Gln Leu Ile Gly Tyr Tyr Ser Pro Ile Thr Leu
        930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Gly Leu Val Ile Glu Arg Arg Leu Ser Asp Lys
            980                 985                 990

His Phe Val Phe Met Gly His Ile Ile Asn Lys Leu Cys Leu Ile Ala
        995                 1000                1005

Gly Gly Thr Gly Val Ala Pro Met Leu Gln Ile Ile Lys Ala Ala
    1010                1015                1020

Phe Met Lys Pro Phe Ile Asp Thr Leu Glu Ser Val His Leu Ile
    1025                1030                1035

Tyr Ala Ala Glu Asp Val Thr Glu Leu Thr Tyr Arg Glu Val Leu
    1040                1045                1050

Glu Glu Arg Arg Arg Glu Ser Arg Gly Lys Phe Lys Lys Thr Phe
    1055                1060                1065

Val Leu Asn Arg Pro Pro Leu Trp Thr Asp Gly Val Gly Phe
    1070                1075                1080

Ile Asp Arg Gly Ile Leu Thr Asn His Val Gln Pro Pro Ser Asp
    1085                1090                1095

Asn Leu Leu Val Ala Ile Cys Gly Pro Pro Val Met Gln Arg Ile
    1100                1105                1110

Val Lys Ala Thr Leu Lys Thr Leu Gly Tyr Asn Met Asn Leu Val
    1115                1120                1125

Arg Thr Val Asp Glu Thr Glu Pro Ser Gly Ser
    1130                1135

<210> SEQ ID NO 23
<211> LENGTH: 3421
<212> TYPE: DNA
<213> ORGANISM: Artificial sequence
<220> FEATURE:
<223> OTHER INFORMATION: cpo nt FRDg T. brucei lacking nt coding for
      C-terminal SKI

<400> SEQUENCE: 23
atggttgatg gtagatcttc tgcttccatt gttgccgttg acccagaaag agctgccaga     60
gaaagagatg ctgctgccag agctttgttg caagactctc cattgcacac caccatgcaa    120
tacgctacct ctggtttgga attgactgtt ccatacgctt tgaaggttgt tgcttctgct    180
gacactttcg acagagccaa ggaagttgct gatgaagtct tgagatgtgc ctggcaattg    240
gctgacaccg ttttgaactc tttcaaccca aactctgaag tctctttagt cggtagatta    300
ccagtcggtc aaaagcatca aatgtctgct ccattgaaac gtgtcatggc ttgttgtcaa    360
agagtctaca actcctctgc tggttgtttc gacccatcca ctgctccagt tgccaaggct    420

```
ttgagagaaa ttgctttggg taaggaaaga aacaatgctt gtttggaagc tttgactcaa    480
gcttgtacct tgccaaactc tttcgtcatt gatttcgaag ctggtactat ctccagaaag    540
cacgaacacg cttctttgga tttgggtggt gtttccaagg gttacatcgt cgattacgtc    600
attgacaaca tcaatgctgc tggtttccaa aacgttttct ttgactgggg tggtgactgt    660
cgtgcctccg gtatgaacgc cagaaacact ccatggggttg tcggtatcac tagacctcct    720
tccttggaca tgttgccaaa ccctccaaag gaagcttctt acatctccgt catctctttg    780
gacaatgaag ctttggctac ctctggtgat tacgaaaact tgatctacac tgctgacgat    840
aaaccattga cctgtaccta cgattggaaa ggtaaggaat tgatgaagcc atctcaatcc    900
aatatcgctc aagtttccgt caagtgttac tctgccatgt acgctgacgc tttggctacc    960
gcttgtttca tcaagcgtga cccagccaag gtcagacaat tgttggatgg ttggagatac   1020
gttagagaca ccgtcagaga ttaccgtgtc tacgtcagag aaaacgaaag agttgccaag   1080
atgttcgaaa ttgccactga agatgctgaa atgagaaaga gaagaatttc caacacttta   1140
ccagctcgtg tcattgttgt tggtggtggt ttggctggtt tgtccgctgc cattgaagct   1200
gctggttgtg gtgctcaagt tgttttgatg gaaaaggaag ccaagttggg tggtaactct   1260
gccaaggcta cctctggtat caacggttgg ggtactagag ctcaagctaa ggcttccatt   1320
gtcgatggtg gtaagtactt cgaaagagat acctacaagt ctggtatcgg tggtaacacc   1380
gatccagctt tggttaagac tttgtccatg aaatctgctg acgctatcgg ttggttgact   1440
tctctaggtg ttccattgac tgttttgtcc caattaggtg gtcactccag aaagagaact   1500
cacagagctc cagacaagaa ggatggtact ccattgccaa ttggtttcac catcatgaaa   1560
actttagaag atcatgttag aggtaacttg tccggtagaa tcaccatcat ggaaaactgt   1620
tccgttacct ctttgttgtc tgaaaccaag gaaagaccag acggtaccaa gcaaatcaga   1680
gttaccggtg tcgaattcac tcaagctggt tctggtaaga ccaccatttt ggctgatgct   1740
gttatcttgg ccaccggtgg tttctccaac gacaagactg ctgattcttt gttgagagaa   1800
catgccccac acttggttaa cttcccaacc accaacggtc catgggctac tggtgatggt   1860
gtcaagttgg ctcaaagatt aggtgctcaa ttggtcgata tggacaaggt tcaattgcac   1920
ccaactggtt tgatcaaccc aaaggaccca gccaacccaa ccaaattctt gggtccagaa   1980
gctctaagag gttctggtgg tgttttgttg aacaaacaag gtaagagatt tgtcaacgaa   2040
ttggatttga gatctgttgt ttccaaggcc atcatggaac aaggtgctga atacccaggt   2100
tctggtggtt ccatgtttgc ttactgtgtc ttgaacgctc tgctcaaaa attgtttggt   2160
gtttcctctc acgaattcta ctggaagaag atgggtttgt tcgtcaaggc tgacaccatg   2220
agagacttgc ctgctttgat tggttgtcca gttgaatccg ttcaacaaac tttagaagaa   2280
tacgaaagat tatccatctc tcaaagatct tgtccaatta ccagaaaatc tgtttaccca   2340
tgtgttttgg gtaccaaagg tccatactat gtcgcctttg tcactccatc tatccactac   2400
accatggggtg gttgtttgat ttctccatct gctgaaatcc aaatgaagaa cacttcttcc   2460
agagctccat gtcccactc caacccaatc ttgggtttat tcggtgctgg tgaagtcacc   2520
ggtggtgtcc acggtggtaa cagattaggt ggtaactctt gttggaatg tgttgttttc   2580
ggtagaattg ccggtgacag agcttctacc attttgcaaa gaaagtcctc tgctttgtct   2640
ttcaaggtct ggaccactgt tgttttgaga gaagtcagag aaggtggtgt ctacggtgct   2700
ggttcccgtg tcttgagatt caacttacca ggtgctctac aaagatctgg tctatccttg   2760
```

| | | |
|---|---|---|
| ggtcaattca ttgccatcag aggtgactgg gacggtcaac aattgattgg ttactactct | 2820 | |
| ccaatcactt tgccagacga tttgggtatg attgacattt tggccagatc tgacaagggt | 2880 | |
| actttacgtg aatggatctc tgctttggaa ccaggtgacg ctgtcgaaat gaaggcttgt | 2940 | |
| ggtggtttgg tcatcgaaag aagattatct gacaagcact tcgttttcat gggtcacatt | 3000 | |
| atcaacaagc tatgtttgat tgctggtggt accggtgttg ctccaatgtt gcaaatcatc | 3060 | |
| aaggccgctt tcatgaagcc attcatcgac actttggaat ccgtccactt gatctacgct | 3120 | |
| gctgaagatg tcactgaatt gacttacaga gaagttttgg aagaacgtcg tcgtgaatcc | 3180 | |
| agaggtaaat tcaagaaaac tttcgttttg aacagacctc ctccattatg gactgacggt | 3240 | |
| gtcggtttca tcgaccgtgg tatcttgacc aaccacgttc aaccaccatc tgacaactta | 3300 | |
| ttggttgcca tctgtggtcc accagttatg caaagaattg tcaaggccac tttaaagact | 3360 | |
| ttaggttaca acatgaactt ggtcagaacc gttgacgaaa ctgaaccatc tggaagttaa | 3420 | |
| g | 3421 | |

<210> SEQ ID NO 24
<211> LENGTH: 1000
<212> TYPE: DNA
<213> ORGANISM: Artificial sequence
<220> FEATURE:
<223> OTHER INFORMATION: TDH3Sc promotor

<400> SEQUENCE: 24

| | | |
|---|---|---|
| ctattttcga ggaccttgtc accttgagcc caagagagcc aagatttaaa ttttcctatg | 60 | |
| acttgatgca aattcccaaa gctaataaca tgcaagacac gtacggtcaa gaagacatat | 120 | |
| ttgacctctt aacaggttca gacgcgactg cctcatcagt aagacccgtt gaaaagaact | 180 | |
| tacctgaaaa aaacgaatat atactagcgt tgaatgttag cgtcaacaac aagaagttta | 240 | |
| atgacgcgga ggccaaggca aaaagattcc ttgattacgt aagggagtta gaatcatttt | 300 | |
| gaataaaaaa cacgcttttt cagttcgagt ttatcattat caatactgcc atttcaagga | 360 | |
| atacgtaaat aattaatagt agtgattttc ctaactttat ttagtcaaaa aattagcctt | 420 | |
| ttaattctgc tgtaacccgt acatgcccaa aataggggc gggttacaca gaatatataa | 480 | |
| catcgtaggt gtctgggtga acagtttatt cctggcatcc actaaatata atggagcccg | 540 | |
| cttttttaagc tggcatccag aaaaaaaaag aatcccagca ccaaaatatt gttttcttca | 600 | |
| ccaaccatca gttcataggt ccattctctt agcgcaacta cagagaacag gggcacaaac | 660 | |
| aggcaaaaaa cgggcacaac ctcaatggag tgatgcaacc tgcctggagt aaatgatgac | 720 | |
| acaaggcaat gacccacgc atgtatctat ctcatttct tacaccttct attacttct | 780 | |
| gctctctctg atttggaaaa agctgaaaaa aaaggttgaa accagttccc tgaaattatt | 840 | |
| cccctacttg actaataagt atataaagac ggtaggtatt gattgtaatt ctgtaaatct | 900 | |
| atttcttaaa cttcttaaat tctacttta tagttagtct tttttttagt tttaaaacac | 960 | |
| caagaactta gtttcgaata acacacata aacaaacaaa | 1000 | |

<210> SEQ ID NO 25
<211> LENGTH: 500
<212> TYPE: DNA
<213> ORGANISM: Artificial sequence
<220> FEATURE:
<223> OTHER INFORMATION: TDH3Sc terminator

<400> SEQUENCE: 25

| | | |
|---|---|---|
| gtgaatttac tttaaatctt gcatttaaat aaattttctt tttatagctt tatgacttag | 60 | |

```
tttcaattta tatactattt taatgacatt ttcgattcat tgattgaaag ctttgtgttt     120
tttcttgatg cgctattgca ttgttcttgt cttttttcgcc acatgtaata tctgtagtag    180
atacctgata cattgtggat gctgagtgaa attttagtta ataatggagg cgctcttaat    240
aattttgggg atattggctt ttttttttaa agtttacaaa tgaatttttt ccgccaggat    300
aacgattctg aagttactct tagcgttcct atcggtacag ccatcaaatc atgcctataa    360
atcatgccta tatttgcgtg cagtcagtat catctcatg aaaaaaactc ccgcaatttc    420
ttatagaata cgttgaaaat taaatgtacg cgccaagata agataacata tatctagatg    480
cagtaatata cacagattcc                                                500
```

<210> SEQ ID NO 26
<211> LENGTH: 1180
<212> TYPE: PRT
<213> ORGANISM: Saccharomyces cerevisiae

<400> SEQUENCE: 26

```
Met Ser Ser Ser Lys Lys Leu Ala Gly Leu Arg Asp Asn Phe Ser Leu
1               5                   10                  15

Leu Gly Glu Lys Asn Lys Ile Leu Val Ala Asn Arg Gly Glu Ile Pro
            20                  25                  30

Ile Arg Ile Phe Arg Ser Ala His Glu Leu Ser Met Arg Thr Ile Ala
        35                  40                  45

Ile Tyr Ser His Glu Asp Arg Leu Ser Met His Arg Leu Lys Ala Asp
    50                  55                  60

Glu Ala Tyr Val Ile Gly Glu Glu Gly Gln Tyr Thr Pro Val Gly Ala
65                  70                  75                  80

Tyr Leu Ala Met Asp Glu Ile Ile Glu Ile Ala Lys Lys His Lys Val
                85                  90                  95

Asp Phe Ile His Pro Gly Tyr Gly Phe Leu Ser Glu Asn Ser Glu Phe
            100                 105                 110

Ala Asp Lys Val Val Lys Ala Gly Ile Thr Trp Ile Gly Pro Pro Ala
        115                 120                 125

Glu Val Ile Asp Ser Val Gly Asp Lys Val Ser Ala Arg His Leu Ala
    130                 135                 140

Ala Arg Ala Asn Val Pro Thr Val Pro Gly Thr Pro Gly Pro Ile Glu
145                 150                 155                 160

Thr Val Gln Glu Ala Leu Asp Phe Val Asn Glu Tyr Gly Tyr Pro Val
                165                 170                 175

Ile Ile Lys Ala Ala Phe Gly Gly Gly Gly Arg Gly Met Arg Val Val
            180                 185                 190

Arg Glu Gly Asp Asp Val Ala Asp Ala Phe Gln Arg Ala Thr Ser Glu
        195                 200                 205

Ala Arg Thr Ala Phe Gly Asn Gly Thr Cys Phe Val Glu Arg Phe Leu
    210                 215                 220

Asp Lys Pro Lys His Ile Glu Val Gln Leu Leu Ala Asp Asn His Gly
225                 230                 235                 240

Asn Val Val His Leu Phe Glu Arg Asp Cys Ser Val Gln Arg Arg His
                245                 250                 255

Gln Lys Val Val Glu Val Ala Pro Ala Lys Thr Leu Pro Arg Glu Val
            260                 265                 270

Arg Asp Ala Ile Leu Thr Asp Ala Val Lys Leu Ala Lys Val Cys Gly
        275                 280                 285
```

```
Tyr Arg Asn Ala Gly Thr Ala Glu Phe Leu Val Asp Asn Gln Asn Arg
290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ser Ala Gln Ile Gln Ile
                325                 330                 335

Ala Ala Gly Ala Thr Leu Thr Gln Leu Gly Leu Leu Gln Asp Lys Ile
                340                 345                 350

Thr Thr Arg Gly Phe Ser Ile Gln Cys Arg Ile Thr Thr Glu Asp Pro
        355                 360                 365

Ser Lys Asn Phe Gln Pro Asp Thr Gly Arg Leu Glu Val Tyr Arg Ser
370                 375                 380

Ala Gly Gly Asn Gly Val Arg Leu Asp Gly Gly Asn Ala Tyr Ala Gly
385                 390                 395                 400

Ala Thr Ile Ser Pro His Tyr Asp Ser Met Leu Val Lys Cys Ser Cys
                405                 410                 415

Ser Gly Ser Thr Tyr Glu Ile Val Arg Arg Lys Met Ile Arg Ala Leu
                420                 425                 430

Ile Glu Phe Arg Ile Arg Gly Val Lys Thr Asn Ile Pro Phe Leu Leu
        435                 440                 445

Thr Leu Leu Thr Asn Pro Val Phe Ile Glu Gly Thr Tyr Trp Thr Thr
450                 455                 460

Phe Ile Asp Asp Thr Pro Gln Leu Phe Gln Met Val Ser Ser Gln Asn
465                 470                 475                 480

Arg Ala Gln Lys Leu Leu His Tyr Leu Ala Asp Leu Ala Val Asn Gly
                485                 490                 495

Ser Ser Ile Lys Gly Gln Ile Gly Leu Pro Lys Leu Lys Ser Asn Pro
                500                 505                 510

Ser Val Pro His Leu His Asp Ala Gln Gly Asn Val Ile Asn Val Thr
                515                 520                 525

Lys Ser Ala Pro Pro Ser Gly Trp Arg Gln Val Leu Leu Glu Lys Gly
530                 535                 540

Pro Ser Glu Phe Ala Lys Gln Val Arg Gln Phe Asn Gly Thr Leu Leu
545                 550                 555                 560

Met Asp Thr Thr Trp Arg Asp Ala His Gln Ser Leu Leu Ala Thr Arg
                565                 570                 575

Val Arg Thr His Asp Leu Ala Thr Ile Ala Pro Thr Thr Ala His Ala
                580                 585                 590

Leu Ala Gly Ala Phe Ala Leu Glu Cys Trp Gly Gly Ala Thr Phe Asp
                595                 600                 605

Val Ala Met Arg Phe Leu His Glu Asp Pro Trp Glu Arg Leu Arg Lys
610                 615                 620

Leu Arg Ser Leu Val Pro Asn Ile Pro Phe Gln Met Leu Leu Arg Gly
625                 630                 635                 640

Ala Asn Gly Val Ala Tyr Ser Ser Leu Pro Asp Asn Ala Ile Asp His
                645                 650                 655

Phe Val Lys Gln Ala Lys Asp Asn Gly Val Asp Ile Phe Arg Val Phe
                660                 665                 670

Asp Ala Leu Asn Asp Leu Glu Gln Leu Lys Val Gly Val Asn Ala Val
                675                 680                 685

Lys Lys Ala Gly Gly Val Val Glu Ala Thr Val Cys Tyr Ser Gly Asp
690                 695                 700

Met Leu Gln Pro Gly Lys Lys Tyr Asn Leu Asp Tyr Tyr Leu Glu Val
```

-continued

```
            705                 710                 715                 720
        Val Glu Lys Ile Val Gln Met Gly Thr His Ile Leu Gly Ile Lys Asp
                        725                 730                 735
        Met Ala Gly Thr Met Lys Pro Ala Ala Ala Lys Leu Leu Ile Gly Ser
                        740                 745                 750
        Leu Arg Thr Arg Tyr Pro Asp Leu Pro Ile His Val His Ser His Asp
                        755                 760                 765
        Ser Ala Gly Thr Ala Val Ala Ser Met Thr Ala Cys Ala Leu Ala Gly
                        770                 775                 780
        Ala Asp Val Val Asp Val Ala Ile Asn Ser Met Ser Gly Leu Thr Ser
        785                 790                 795                 800
        Gln Pro Ser Ile Asn Ala Leu Leu Ala Ser Leu Glu Gly Asn Ile Asp
                        805                 810                 815
        Thr Gly Ile Asn Val Glu His Val Arg Glu Leu Asp Ala Tyr Trp Ala
                        820                 825                 830
        Glu Met Arg Leu Leu Tyr Ser Cys Phe Glu Ala Asp Leu Lys Gly Pro
                        835                 840                 845
        Asp Pro Glu Val Tyr Gln His Glu Ile Pro Gly Gly Gln Leu Thr Asn
        850                 855                 860
        Leu Leu Phe Gln Ala Gln Gln Leu Gly Leu Gly Glu Gln Trp Ala Glu
        865                 870                 875                 880
        Thr Lys Arg Ala Tyr Arg Glu Ala Asn Tyr Leu Leu Gly Asp Ile Val
                        885                 890                 895
        Lys Val Thr Pro Thr Ser Lys Val Val Gly Asp Leu Ala Gln Phe Met
                        900                 905                 910
        Val Ser Asn Lys Leu Thr Ser Asp Asp Ile Arg Arg Leu Ala Asn Ser
                        915                 920                 925
        Leu Asp Phe Pro Asp Ser Val Met Asp Phe Phe Glu Gly Leu Ile Gly
                        930                 935                 940
        Gln Pro Tyr Gly Gly Phe Pro Glu Pro Leu Arg Ser Asp Val Leu Arg
        945                 950                 955                 960
        Asn Lys Arg Arg Lys Leu Thr Cys Arg Pro Gly Leu Glu Leu Glu Pro
                        965                 970                 975
        Phe Asp Leu Glu Lys Ile Arg Glu Asp Leu Gln Asn Arg Phe Gly Asp
                        980                 985                 990
        Ile Asp Glu Cys Asp Val Ala Ser Tyr Asn Met Tyr Pro Arg Val Tyr
                        995                 1000                1005
        Glu Asp Phe Gln Lys Ile Arg Glu Thr Tyr Gly Asp Leu Ser Val
        1010                1015                1020
        Leu Pro Thr Lys Asn Phe Leu Ala Pro Ala Glu Pro Asp Glu Glu
        1025                1030                1035
        Ile Glu Val Thr Ile Glu Gln Gly Lys Thr Leu Ile Ile Lys Leu
        1040                1045                1050
        Gln Ala Val Gly Asp Leu Asn Lys Lys Thr Gly Gln Arg Glu Val
        1055                1060                1065
        Tyr Phe Glu Leu Asn Gly Glu Leu Arg Lys Ile Arg Val Ala Asp
        1070                1075                1080
        Lys Ser Gln Asn Ile Gln Ser Val Ala Leu Pro Lys Ala Asp Val
        1085                1090                1095
        His Asp Thr His Gln Ile Gly Ala Pro Met Ala Gly Val Ile Ile
        1100                1105                1110
        Glu Val Lys Val His Lys Gly Ser Leu Val Lys Lys Gly Glu Ser
        1115                1120                1125
```

```
Ile Ala Val Leu Ser Ala Met Lys Met Glu Met Val Val Ser Ser
        1130                1135                1140

Pro Ala Asp Gly Gln Val Lys Asp Val Phe Ile Lys Asp Gly Glu
    1145                1150                1155

Ser Val Asp Ala Ser Asp Leu Leu Val Val Leu Glu Glu Glu Thr
    1160                1165                1170

Leu Pro Pro Ser Gln Lys Lys
    1175                1180

<210> SEQ ID NO 27
<211> LENGTH: 3543
<212> TYPE: DNA
<213> ORGANISM: Saccharomyces cerevisiae

<400> SEQUENCE: 27
atgagcagta gcaagaaatt ggccggtctt agggacaatt tcagtttgct cggcgaaaag      60
aataagatct tggtcgccaa tagaggtgaa attccgatta gaattttttag atctgctcat    120 gagctgtcta tgagaaccat cgccatatac tcccatgagg accgtctttc aatgcacagg    180
ttgaaggcgg acgaagcgta tgttatcggg gaggagggcc agtatacacc tgtgggtgct    240
tacttggcaa tggacgagat catcgaaatt gcaagaaagc ataaggtgga tttcatccat    300
ccaggttatg ggttcttgtc tgaaaattcg gaatttgccg acaaagtagt gaaggccggt    360
atcacttgga tcggccctcc agctgaagtt attgactctg tgggtgacaa agtctctgcc    420
agacacttgg cagcaagagc taacgttcct accgttcccg gtactccagg acctatcgaa    480
actgtgcaag aggcacttga cttcgttaat gaatacggct acccggtgat cattaaggcc    540
gcctttggtg gtggtggtag aggtatgaga gtcgttagag aaggtgacga cgtggcagat    600
gcctttcaac gtgctaccct cgaagcccgt actgccttcg gtaatggtac ctgctttgtg    660
gaaagattct tggacaagcc aaagcatatt gaagttcaat gttggctgaa taaccacgga    720
aacgtggttc atcttttcga aagagactgt tctgtgcaaa gaagacacca aaaagttgtc    780
gaagtcgctc cagcaaagac tttgccccgt gaagttcgtg acgctatttt gacagatgct    840
gttaaattag ctaaggtatg tggttacaga acgcaggta ccgccgaatt cttggttgac    900
aaccaaaaca gacactattt cattgaaatt aatccaagaa ttcaagtgga gcataccatc    960
actgaagaaa tcaccggtat tgacattgtt tctgcccaaa tccagattgc cgcaggtgcc   1020
actttgactc aactaggtct attacaggat aaaatcacca cccgtgggtt ttccatccaa   1080
tgtcgtatta ccactgaaga tccctctaag aatttccaac cggataccgg tcgcctggag   1140
gtctatcgtt ctgccggtgg taatggtgtg agattggacg tggtaacgc ttatgcaggt   1200 gctactatct cgcctcacta cgactcaatg ctggtcaaat gttcatgctc tggttctact   1260
tatgaaatcg tccgtaggaa gatgattcgt gccctgatcg aattcagaat cagaggtgtt   1320
aagaccaaca ttcccttcct attgactctt ttgaccaatc cagttttttat tgagggtaca   1380 tactggacga cttttattga cgacaccccca caactgttcc aaatggtatc gtcacaaaac   1440
agagcgcaaa aactgttaca ctatttggca gacttggcag ttaacggttc ttctattaag   1500
ggtcaaattg gcttgccaaa actaaaatca atccaagtg tcccccattt gcacgatgct   1560
cagggcaatg tcatcaacgt tacaaagtct gcaccaccat ccggatggag acaagtgcta   1620
ctggaaaagg gaccatctga atttgccaag caagtcagac agttcaatgg tactctactg   1680
atggacacca cctggagaga cgctcatcaa tctctacttg caacaagagt cagaacccac   1740
```

```
gatttggcta caatcgctcc aacaaccgca catgcccttg caggtgcttt cgctttagaa    1800
tgttggggtg gtgctacatt cgacgttgca atgagattct tgcatgagga tccatgggaa    1860
cgtctgagaa aattaagatc tctggtgcct aatattccat tccaaatgtt attacgtggt    1920
gccaacggtg tggcttactc ttcattacct gacaatgcta ttgaccattt tgtcaagcaa    1980
gccaaggata atggtgttga tatatttaga gttttttgatg ccttgaatga tttagaacaa    2040
ttaaaagttg gtgtgaatgc tgtcaagaag gccggtggtg ttgtcgaagc tactgtttgt    2100
tactctggtg acatgcttca gccaggtaag aaatacaact tagactacta cctagaagtt    2160
gttgaaaaaa tagttcaaat gggtacacat atcttgggta ttaaggatat ggcaggtact    2220
atgaaaccgg ccgctgccaa attattaatt ggctccctaa gaaccagata tccggattta    2280
ccaattcatg ttcacagtca tgactccgca ggtactgctg ttgcgtctat gactgcatgt    2340
gccctagcag gtgctgatgt tgtcgatgta gctatcaatt caatgtcggg cttaacttcc    2400
caaccatcaa ttaatgcact gttggcttca ttagaaggta acattgatac tgggattaac    2460
gttgagcatg ttcgtgaatt agatgcatac tgggccgaaa tgagactgtt gtattcttgt    2520
ttcgaggccg acttgaaggg accagatcca gaagtttacc aacatgaaat cccaggtggt    2580
caattgacta acttgttatt ccaagctcaa caactgggtc ttggtgaaca atgggctgaa    2640
actaaaagag cttacagaga agccaattac ctactgggag atattgttaa agttacccca    2700
acttctaagg ttgtcggtga tttagctcaa ttcatggttt ctaacaaact gacttccgac    2760
gatattagac gtttagctaa ttctttggac tttcctgact ctgttatgga ctttttttgaa    2820 ggtttaattg gtcaaccata cggtgggttc ccagaaccat taagatctga tgtattgaga    2880
aacaagagaa gaaagttgac gtgccgtcca ggtttagaat tagaaccatt tgatctcgaa    2940
aaaattgagg aagacttgca gaacagattc ggtgatattg atgaatgcga tgttgcttct    3000
tacaatatgt atccaagggt ctatgaagat ttccaaaaga tcagagaaac atacggtgat    3060
ttatcagttc taccaaccaa aaatttccta gcaccagcag aacctgatga agaaatcgaa    3120
gtcaccatcg aacaaggtaa gactttgatt atcaaattgc aagctgttgg tgacttaaat    3180
aagaaaactg gcaaagaga agtgtatttt gaattgaacg tgaattaag aaagatcaga    3240 gttgcagaca agtcacaaaa catacaatct gttgctaaac caaaggctga tgtccacgat    3300
actcaccaaa tcggtgcacc aatggctggt gttatcatag aagttaaagt acataaaggg    3360 tcttttggtga aaaagggcga atcgattgct gttttgagtg ccatgaaaat ggaaatggtt    3420
gtctcttcac cagcagatgg tcaagttaaa gacgttttca ttaaggatgg tgaaagtgtt    3480
gacgcatcag atttgttggt tgtcctagaa gaagaaaccc tacccccatc ccaaaaaaag    3540
taa                                                                  3543
```

<210> SEQ ID NO 28
<211> LENGTH: 30
<212> TYPE: DNA
<213> ORGANISM: Artificial sequence
<220> FEATURE:
<223> OTHER INFORMATION: P1 primer

<400> SEQUENCE: 28
ggactagtat gagcagtagc aagaaattgg                                       30

<210> SEQ ID NO 29
<211> LENGTH: 31
<212> TYPE: DNA
<213> ORGANISM: Artificial sequence -continued

```
<220> FEATURE:
<223> OTHER INFORMATION: P2 primer

<400> SEQUENCE: 29
ccgctcgagt tactttttt gggatggggg t                                    31
```